US006919077B2

(12) United States Patent
Kapustay et al.

(10) Patent No.: US 6,919,077 B2
(45) Date of Patent: Jul. 19, 2005

(54) LFA-1 ALPHA SUBUNIT ANTIBODIES AND METHODS OF USE

(75) Inventors: Pamela M. Kapustay, Thousand Oaks, CA (US); Rex H. Lewis, Las Vegas, NV (US)

(73) Assignee: Aids Research, LLC, Las Vegas, NV (US)

( * ) Notice: Subject to any disclaimer, the term of this patent is extended or adjusted under 35 U.S.C. 154(b) by 208 days.

(21) Appl. No.: 10/261,164

(22) Filed: Sep. 27, 2002

(65) Prior Publication Data

US 2004/0062765 A1 Apr. 1, 2004

(51) Int. Cl.[7] ............................................. A61K 39/395
(52) U.S. Cl. ............................... 424/130.1; 424/135.1; 424/139.1; 424/141.1; 424/142.1; 424/143.1; 424/144.1; 424/154.1
(58) Field of Search ........................... 424/130.1, 135.1, 424/139.1, 141.1, 142.1, 143.1, 144.1, 154.1

(56) References Cited

U.S. PATENT DOCUMENTS

| 5,002,869 A | | 3/1991 | Schlossman |
| 5,424,066 A | * | 6/1995 | Allen ....................... 424/144.1 |
| 5,651,970 A | | 7/1997 | Allen |

OTHER PUBLICATIONS

Cruse et al. Illustrated Dictionary of Immunology (Boca Raton, FL, CRC Press, Inc., 1995), p. 143. QR180.4.C78.*
Sawyer, "Cytolin: Hype–Driven Therapy", *GMHC Treatment Issues,* Dec. 1995; 9(12): HADAM Re: S6F1 Antibody. Internet message board, Apr. 1, 1998.
Sanchez–Madrid, et al., "Three Distinct Antigens Associated With Human T–lymphocyte–mediated Cytolysis: LFA–1, LFA–2, and LFA–3," *Immunology,* Dec., 1982, vol. 79, pp. 7489–7493.
Zang, et al. "The Top of the Inserted–like Domain of the Integrin Lymphocyte Function–associated Antigen–1 β Subunit Contacts the α Subunit β–Propeller Domain near β–Sheet 3," *The Journal of Biological Chemistry,* Jul. 21, 2000, vol. 275, No. 29, pp. 22202–22212.
Morimoto, et al. "A novel epitope of the LFA–1 antigen which can distinguish killer effector and suppressor cells in human CD8 cells," *Nature,* Dec., 1987, vol. 330, pp. 479–482.
Huang and Springer, "Folding of the β–propeller domain of the integrin αL subunit is independent of the I domain and dependent on the β2 subunit," *Immunology,* Apr., 1997, vol. 94., pp. 3162–3167.
Allen, et al. , "Leukocyte Adhesion Molecules as a Cofactor in AIDS: Basic Science and Pilot Study," *Medical Hypotheses,* 1995, pp. 164–168.
Allen, et al., "Immunization Against the HIV–Associated Anti–Self, Anti–CD4 Cytotoxic T Lymphocyte," 1993, *AIDS,* vol. 7, No. 8, pp. 1130–1131.
Hildreth, et al., "A human lymphocyte–associated antigen involved in cell–mediated lympholysis," *Eur. J. Immunology,* 1983, vol. 13, pp. 202–208.
Paquette, et al., "Level of ICAM–1 Surface Expression on Virus Producer Cells Influences both the Amount of Virion–Bound Host ICAM–1 and Human Immunodeficiency Virus Type 1 Infectivity, " *Journal of Virology,* Nov. 1998, vol. 72, No. 11, pp. 9329–9336.
Talento, et al., "A Single Administration of LFA–1 Antibody Confers Prolonged Allograft Survival," *Transplantation,* Feb. 1993, vol. 55, No. 2, pp. 418–422.
Cavallin, et al., "Phenotypical and functional evaluation of CD8+/S6F1+ T lymphocytes in haemophiliac individuals with HIV–1 infection," *Clin. Exp. Immunology* 1993, vol. 93, pp. 51–55.
Edwards, et al., "Mapping the Intercellular Adhesion Molecule–1 and –2 Binding Site on the Inserted Domain of Leukocyte Function–associated Antigen–1," *Journal of Biological Chemistry,* Oct. 30, 1998, vol. 273, Issue 44.
Edwards, et al. "Identification of Amino Acids in the CD11a I–domain Important for Binding of the Leukocyte Function–associated Antigen–1 (LFA–1) to Intercellular Adhesion Molecule–1 (ICAM–1)" *The American Society for the Biochemistry and Molecular Biology, Inc. ,* May 26, 1995, vol. 270, No. 21, pp. 12635–12640.
Binnerts, et al., "Antibodies That Selectively Inhibit Leukocyte Function–associated Antigen 1 Binding to Intercellular Adhesion Molecule–3 Recognize a Unique Epitope Within the CD11a I Domain" *The American Society for the Biochemistry and Molecular Biology, Inc.,* Apr. 26, 1996, vol. 271, No. 17, pp. 9962–9968.

* cited by examiner

*Primary Examiner*—Jeffrey Stucker
(74) *Attorney, Agent, or Firm*—Pillsbury Winthrop LLP

(57) ABSTRACT

Antibodies useful for and methods of treating LFA-1 alpha subunit associated physiological conditions and diseases treatable with an antibody that binds LFA-1 alpha subunit, such as HIV, are provided.

107 Claims, 6 Drawing Sheets

MKDSCITVMAMALLSGFFFFAPASSYNLDVRGARSFSPPRAGRHFGYRVLQVGNGVIV
GAPGEGNSTGSLYQCQSGTGHCLPVTLRGSNYTSKYLGMTLATDPTDGSILACDPGLS
RTCDQNTYLSGLCYLFRQNLQGPMLQGRPGFQECIKGNVDLVFLFDGSMSLQPDEFQK
ILDFMKDVMKKLSNTSYQFAAVQFSTSYKTEFDFSDYVKWKDPDALLKHVKHMLLLTN
TFGAINYVATEVFREELGARPDATKVLIIITDGEATDSGNIDAAKDIIRYIIGIGKHF
QTKESQETLHKFASKPASEFVKILDTFEKLKDLFTELQKKIYVIEGTSKQDLTSFNME
LSSSGISADLSRGHAVVGAVGAKDWAGGFLDLKADLQDDTFIGNEPLTPEVRAGYLGY
TVTWLPSRQKTSLLASGAPRYQHMGRVLLFQEPQGGGHWSQVQTIHGTQIGSYFGGEL
CGVDVDQDGETELLLIGAPLFYGEQRGGRVFIYQRRQLGFEEVSELQGDPGYPLGRFG
EAITALTDINGDGLVDVAVGAPLEEQGAVYIFNGRHGGLSPQPSQRIEGTQVLSGIQW
FGRSIHGVKDLEGDGLADVAVGAESQMIVLSSRPVVDMVTLMSFSPAEIPVHEVECSY
STSNKMKEGVNITICFQIKSLYPQFQGRLVANLTYTLQLDGHRTRRRGLFPGGRHELR
RNIAVTTSMSCTDFSFHFPVCVQDLISPINVSLNFSLWEEEGTPRDQRAQGKDIPPIL
RPSLHSETWEIPFEKNCGEDKKCEANLRVSFSPARSRALRLTAFASLSVELSLSNLEE
DAYWVQLDLHFPPGLSFRKVEMLKPHSQIPVSCEELPEESRLLSRALSCNVSSPIFKAG
HSVALQMMFNTLVNSSWGDSVELHANVTCNNEDSDLLEDNSATTIIPILYPINILIQDQ
EDSTLYVSFTPKGPKIHQVKHMYQVRIQPSIHDHNIPTLEAVVGVPQPPSEGPITHQWS
VQMEPPVPCHYEDLERLPDAAEPCLPGALFRCPVVFRQEILVQVIGTLELVGEIEASSM
FSLCSSLSISFNSSKHFHLYGSNASLAQVVMKVDVVYEKQMLYLYVLSGIGGLLLLLLI
FIVLYKVGFFKRNLKEKMEAGRGVPNGIPAEDSEQLASGQEAGDPGCLKPLHEKDSESG
GGKD (SEQ ID NO:1)

YNLDVRGARSFSPPRAGRHFGYRVLQVGNGVIVGAPGEGNSTGSLYQCQSGTGHCLPVTL
RGSNYTSKYLGMTLATDPTDGSILACDPGLSRTCDQNTYLSGLCYLFRQNLQGPMLQGRP
GFQECIKGNVDLVFLFDGSMSLQPDEFQKILDFMKDVMKKLSNTSYQFAAVQFSTSYKTE
FDFSDYVKWKDPDALLKHVKHMLLLTNTFGAINYVATEVFREELGARPDATKVLIIITDG
EATDSGNIDAAKDIIRYIIGIGKHFQTKESQETLHKFASKPASEFVKILDTFEKLKDLFT
ELQKKIYVIEGTSKQDLTSFNMELSSSGISADLSRGHAVVGAVGAKDWAGGFLDLKAD

Figure 4

LQDDTFIGNEPLTPEVRAGYLGYTVTWLPSRQKTSLLASGAPRYQHMGRVLLFQEPQG

GGHWSQVQTIHGTQIGSYFGGELCGVDVDQDGETELLLIGAPLFYGEQRGGRVFIYQR

RQLGPEEVSELQGDPGYPLGRFGEAITALTDINGDGLVDVAVGAPLEEQGAVYIFNGR

HGGLSPQPSQRIEGTQVLSGIQWFGRSIHGVKDLEGDGLADVAVGAESQMIVLSSRP (SEQ ID NO:2)

```
   1 cctctttcac cctgtctagg ttgccagcaa atcccacggg cctcctgacg ctgcccctgg
  61 ggccacaggt ccctcgagtg ctggaaggat gaaggattcc tgcatcactg tgatggccat
 121 ggcgctgctg tctgggttct ttttcttcgc gccggcctcg agctacaacc tggacgtgcg
 181 gggcgcgcgg agcttctccc caccgcgcgc gggaggcac tttggatacc gcgtcctgca
 241 ggtcggaaac ggggtcatcg tgggagctcc aggggagggg aacagcacag gaagcctcta
 301 tcagtgccag tcgggcacag gacactgcct gccagtcacc ctgagaggtt ccaactatac
 361 ctccaagtac ttgggaatga ccttggcaac agacccaca gatggaagca ttttggcctg
 421 tgaccctggg ctgtctcgaa cgtgtgacca gaacacctat ctgagtggcc tgtgttacct
 481 cttccgccag aatctgcagg gtcccatgct gcaggggcgc cctggttttc aggaatgtat
 541 caagggcaac gtagacctgg tatttctgtt tgatggttcg atgagcttgc agccagatga
 601 atttcagaaa attctggact tcatgaagga tgtgatgaag aaactcagca cacttcgta
 661 ccagtttgct gctgttcagt tttccacaag ctacaaaaca gaatttgatt tctcagatta
 721 tgttaaatgg aaggaccctg atgctctgct gaagcatgta aagcacatgt tgctgttgac
 781 caatacctt ggtgccatca attatgtcgc gacagaggtg ttccgggagg agctggggc
 841 ccggccagat gccaccaaag tgcttatcat catcacggat ggggaggcca ctgacagtgg
 901 caacatcgat gcggccaaag acatcatccg ctacatcatc gggattggaa agcatttca
 961 gaccaaggag agtcaggaga ccctccacaa atttgcatca aaacccgcga gcgagtttgt
1021 gaaaattctg gacacatttg agaagctgaa agatctattc actgcagctgc agaagaagat
1081 ctatgtcatt gagggcacaa gcaaacagga cctgacttcc ttcaacatgg agctgtcctc
1141 cagcggcatc agtgctgacc tcagcagggg ccatgcagtc gtgggggcag taggagccaa
1201 ggactgggct ggggcttc ttgacctgaa ggcagacctg caggatgaca catttattgg
1261 gaatgaacca ttgacaccag aagtgagagc aggctatttg ggttacaccg tgacctggct
1321 gccctcccgg caaaagactt cgttgctggc ctcgggagcc cctcgatacc agcacatggg
1381 ccgagtgctg ctgttccaag agccacaggg cggaggacac tggagccagg tccagacaat
1441 ccatgggacc cagattggct cttatttcgg tggggagctg tgtggcgtcg acgtggacca
1501 agatggggag acagagctgc tgctgattgg tgccccactg ttctatgggg agcagagagg
1561 aggccgggtg tttatctacc agagaagaca gttgggtt gaagaagtct cagagctgca
1621 gggggacccc ggctacccac tcgggcggtt tggagaagcc atcactgctc tgacagacat
1681 caacggcgat gggctggtag acgtggctgt ggggccct ctggaggagc aggggctgt
1741 gtacatcttc aatgggaggc acgggggct tagtccccag ccaagtcagc ggatagaagg
1801 gacccaagtg ctctcaggaa ttcagtggtt tggacgctcc atccatgggg tgaaggacct
1861 tgaaggggat ggcttggcag atgtggctgt ggggctgag agccagatga tcgtgctgag
1921 ctcccggccc gtggtggata tggtcaccct gatgtcttc tctccagctg agatcccagt
1981 gcatgaagtg gagtgctcct attcaaccag taacaagatg aaagaaggag ttaatatcac
2041 aatctgtttc cagatcaagt ctctctaccc ccagttccaa ggccgcctgg ttgccaatct
2101 cacttacact ctgcagctgg atggccaccg gaccagaaga cggggttgt tcccaggagg
2161 gagacatgaa ctcagaagga atatagctgt caccaccagc atgtcatgca ctgacttctc
2221 atttcatttc ccggtatgtg ttcaagacct catctccccc atcaatgttt ccctgaattt
2281 ctctctttgg gaggaggaag ggacaccgag ggaccaaagg gcgcagggca aggacatacc
2341 gcccatcctg agacctccc tgcactcgga aacctgggag atccctttg agaagaactg
2401 tggggaggac aagaagtgtg aggcaaactt gagagtgtcc ttctctcctg caagatccag
2461 agccctgcgt ctaactgctt ttgccagcct ctctgtggag ctgagcctga gtaacttgga
2521 agaagatgct tactgggtcc agctggacct gcacttcccc ccgggactct ccttccgcaa
2581 ggtggagatg ctgaagcccc atagccagat acctgtgagc tgcgaggagc ttcctgaaga
2641 gtccaggctt ctgtccaggg cattatcttg caatgtgagc tctcccatct tcaaagcagg
2701 ccactcggtt gctctgcaga tgatgtttaa tacactggta aacagctcct gggggactc
2761 ggttgaattg cacgccaatg tgacctgtaa caatgaggac tcagacctcc tggaggacaa
```

FIG. 4-1

```
2821 ctcagccact accatcatcc ccatcctgta ccccatcaac atcctcatcc aggaccaaga
2881 agactccaca ctctatgtca gtttcacccc caaaggcccc aagatccacc aagtcaagca
2941 catgtaccag gtgaggatcc agccttccat ccacgaccac aacataccca ccctggaggc
3001 tgtggttggg gtgccacagc ctcccagcga ggggcccatc acacaccagt ggagcgtgca
3061 gatggagcct cccgtgccct gccactatga ggatctggag aggctcccgg atgcagctga
3121 gccttgtctc cccggagccc tgttccgctg ccctgttgtc ttcaggcagg agatcctcgt
3181 ccaagtgatc gggactctgg agctggtggg agagatcgag gcctcttcca tgttcagcct
3241 ctgcagctcc ctctccatct ccttcaacag cagcaagcat ttccacctct atggcagcaa
3301 cgcctccctg gcccaggttg tcatgaaggt tgacgtggtg tatgagaagc agatgctcta
3361 cctctacgtg ctgagcggca tcggggggct gctgctgctg ctgctcattt tcatagtgct
3421 gtacaaggtt ggtttcttca acggaacct gaaggagaag atggaggctg cagaggtgt
3481 cccgaatgga atccctgcag aagactctga gcagctggca tctgggcaag aggctgggga
3541 tcccggctgc ctgaagcccc tccatgagaa ggactctgag agtggtggtg caaggactg
3601 agtccaggcc tgtgaggtgc agagtccca gaactggact caggatgccc agggccactc
3661 tgcctctgcc tgcattctgc cgtgtgccct cgggcgagtc actgcctctc cctggccctc
3721 agtttcccta tctcgaacat ggaactcatt cctgaatgtc tcctttgcag gctcataggg
3781 aagacctgct gagggaccag ccaagagggc tgcaaagtg agggcttgtc attaccagac
3841 ggttcaccag cctctcttgg ttccttcctt ggaagagaat gtctgatcta aatgtggaga
3901 aactgtagtc tcaggaccta gggatgttct ggccctcacc cctgcctgg gatgtccaca
3961 gatgcctcca cccccagaa cctgtccttg cacactccc tgcactggag tccagtctct
4021 tctgctggca gaaagcaaat gtgacctgtg tcactacgtg actgtggcac acgccttgtt
4081 cttggccaaa gaccaaattc cttggcatgc cttccagcac cctgcaaaat gagaccctcg
4141 tggccttccc cagcctcttc tagagccgtg atgcctccct gttgaagctc tggtgacacc
4201 agcctttctc ccaggccagg ctccttcctg tcttcctgca ttcacccaga cagctccctc
4261 tgcctgaacc ttccatctcg cccacccctc cttccttgac cagcagatcc cagctcacgt
4321 cacacacttg gtgggtcct cacatctttc acttccac cacctgcac tactccctca
4381 aagcacacgt catgtttctt catccggcag cctggatgtt ttttccctgt ttaatgattg
4441 acgtacttag cagctatctc tcagtgaact gtgagggtaa aggctatact tgtcttgttc
4501 accttgggat gacgccgcat gatatgtcag ggcgtgggac atctagtagg tgcttgacat
4561 aatttcactg aattaatgac agagccagtg ggaagataca gaaaagagg gccggggctg
4621 ggcgcggtgg ttcacgcctg taatcccagc actttgggag gccaaggagg gtggatcacc
4681 tgaggtcagg agttagaggc cagcctggcg aaaccccatc tctactaaaa atacaaaatc
4741 caggcgtggt ggcacacacc tgtagtccca gctactcagg aggttgaggt aggagaattg
4801 cttgaacctg ggaggtggag gttgcagtga gccaagattg cgccattgca ctccagcctg
4861 ggcaacacag cgagactccg tctcaaggaa aaaataaaaa taaaaagcgg gcacggcgcc
4921 ggacatcccc acccttggag gctgtcttct caggctctgc cctgccctag ctccacaccc
4981 tctcccagga cccatcacgc ctgtgcagtg gccccacag aaagactgag ctcaaggtgg
5041 gaaccacgtc tgctaacttg gagccccagt gccaagcaca gtgcctgcat gtatttatcc
5101 aataaatgtg aaattctgtc caaaaaaaa aaa   (SEQ ID NO:3)
```

FIG. 4-2

LFA-1 ALPHA SUBUNIT ANTIBODIES AND METHODS OF USE

TECHNICAL FIELD

The invention relates to antibodies useful for treating LFA-1 alpha subunit associated physiological conditions and diseases treatable with an antibody that binds LFA-1 alpha subunit, such as HIV.

BACKGROUND

Human lymphocyte function-associated antigen (LFA)-1 is a heterodimeric lymphocyte surface glycoprotein and a member of the integrin family. It has a broad distribution and is present on cells of the lymphocytic, granulocytic, and monocyte series. LFA-1 functions primarily as an adhesion molecule, mediating cell-cell interactions in inflammation playing an important role in cytotoxic T lymphocyte (CTL)-mediated cell lysis by enabling the formation of conjugates between CTLs and their target cells.

Animal and human studies have confirmed a role for adhesion molecules in a variety of pathological processes, including chronic viral hepatitis, transplant rejection, septic shock, immunologically-mediated lung and kidney disease and other autoimmune disorders. Studies suggest that the expression of these adhesion molecules may be a useful marker for active inflammation under certain conditions and that abrogation of endothelial adhesion by interfering with such molecules may inhibit tissue injury.

The role of adhesion molecules in HIV disease has been demonstrated. Adhesion molecules are involved in different stages of HIV-1 infection and affect HIV-1 neutralization by virus-specific antibodies. In cell-to-cell interactions, the presence of LFA-1 was found to be crucial for virus-mediated syncytium formation. In cell-free viral transmission, LFA-1 particles incorporated into the virion retain their biological functions and have been shown to increase virus-cell interaction, enhance virus infectivity, and extend the host cell range of the virus. In addition, it has been reported that neutralizing activities of both HIV+ plasma and human anti-gp120 monoclonal antibodies are enhanced by an anti-LFA-1 monoclonal antibody capable of blocking LFA-1 functions.

Adhesion molecules are expressed on CD8+ cytotoxic-T lymphocytes (CTLs) prevalent in individuals with HIV infection. Given their role in CTL-mediated lysis of target cells, LFA-1 may also be involved in the progressive depletion of CD4+ T cell counts in HIV-infected patients. In addition to the cytopathic effects of viral products and the direct killing by HIV-specific CTLs, indirect mechanisms have been proposed to explain T-cell depletion. One particular hypothesis may be the killing of uninfected CD4+ T cells. Several studies have identified a population of non-HLA-restricted CTLs which lyse uninfected activated CD4+ lymphocytes. This population is present only in HIV seropositive individuals, but not in seronegative controls, and its activity has been shown to coincide with a drop in CD4+ lymphocyte numbers in vivo in some individuals.

Several mouse hybridoma lines producing monoclonal antibodies reactive with LFA-1 have been studied. Purportedly, anti-LFA-1 monoclonal antibodies reversibly inhibited CTL killing by slowing the initial rate of cytolysis and by interfering with conjugate formation between effector and target cells.

BRIEF DESCRIPTION OF THE DRAWINGS

FIG. 4 shows exemplary LFA-1 alpha subunit amino acid sequence (SEQ ID NO:1); nucleotide sequence including a coding sequence for exemplary LFA-1 alpha subunit (SEQ ID NO:3); and proposed LFA-1 alpha subunit β-propeller domain amino acid sequence (SEQ ID NO:2).

SUMMARY

Figure 1:
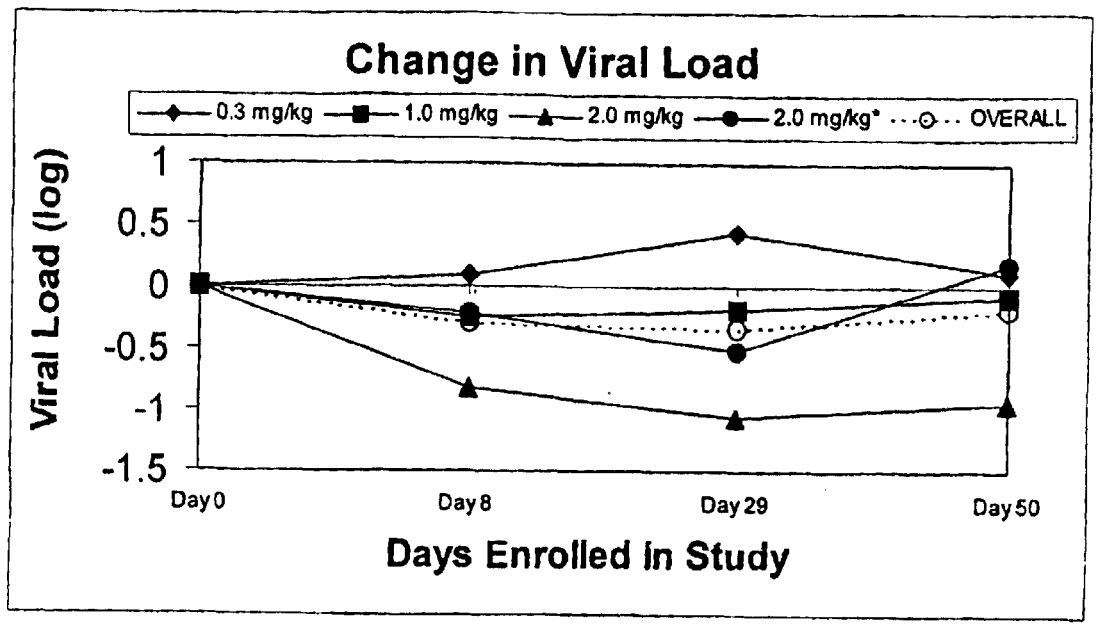
FIG. 1 shows the change in HIV-1 RNA viral load from baseline following administration of the indicated amounts and dose regimens of LFA-1 alpha subunit antibody at days 8, 29, and 50. 2.0 mg/kg* indicates 2.0 mg/kg single-dose group.

The invention provides methods of treating a subject having or at risk of having a physiological condition associated with or caused by decreased CD4+ cell numbers. In one embodiment, a method includes administering to the subject a monoclonal or polyclonal antibody that binds to LFA-1 alpha subunit (CD11a) in an amount greater than 1 mg/kg body weight, for example, greater than 1.25 to 1.5, 1.5 to 1.75, 1.75 to 2.0, 2.0 to 2.5, 2.5 to 3.0, 3.0 to 5.0 mg/kg body weight, or greater. In various aspects, the antibody inhibits binding of S6F 1 or TS2/4 antibody to LFA-1 alpha subunit; binds to an epitope to which S6F1 or TS2/4 antibody binds; is a humanized form of S6F 1 or TS2/4. In further aspects, the antibody binds an epitope including an LFA-1 alpha subunit β-propeller domain, e.g., located all or in a part of amino acids 1 to 57 of LFA-1 alpha subunit, such as all or a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha subunit as set forth in SEQ ID NO:2. In additional aspects, the antibody is a subsequence of full length antibody containing two variable chains and two constant regions, e.g., an Fab, Fab', $(Fab)_2$, Fv or scFv. In yet additional aspects, the antibody that binds to LFA-1 alpha subunit is a humanized form, e.g., having one or more amino acid substitutions, additions or deletions, provided that said antibody has a binding affinity for LFA-1 alpha subunit or an epitope in LFA-1 alpha subunit within about 1 to 3, 2 to 5, 5 to 10, 10 to 50 or 10 to 100 of the binding affinity of S6F1 or TS2/4.

The invention also provides methods of increasing CD4+ cell numbers in a subject. In one embodiment, a method includes administering to the subject an antibody that binds to LFA-1 alpha subunit (CD11a) in an amount greater than 1 mg/kg body weight, for example, greater than 1.25 to 1.5, 1.5 to 1.75, 1.75 to 2.0, 2.0 to 2.5, 2.5 to 3.0, 3.0 to 5.0 mg/kg body weight, or greater. In various aspects, the antibody inhibits binding of S6F1 or TS2/4 antibody to LFA-1 alpha subunit; binds to an epitope to which S6F1 or TS2/4 antibody binds; is a humanized form of S6F1 or TS2/4. In further aspects, the antibody binds an epitope including an LFA-1 alpha subunit β-propeller domain, e.g., located all or in a part of amino acids 1 to 57 of LFA-1 alpha subunit, such as all or a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha subunit as set forth in SEQ ID NO:2. In additional aspects, the antibody is a subsequence of full length antibody containing two variable chains and two constant regions, e.g., an Fab, Fab', $(Fab)_2$, Fv or scFv. In yet additional aspects, the antibody that binds to LFA-1 alpha subunit is a humanized form, e.g., having one or more amino acid substitutions, additions or deletions, provided that said antibody has a binding affinity for LFA-1 alpha subunit or an epitope in LFA-1 alpha subunit within about 1 to 3, 2 to 5, 5 to 10, 10 to 50 or 10 to 100 of the binding affinity of S6F1 or TS2/4.

The invention further provides methods of inhibiting or preventing decreases in CD4+ cell numbers in a subject. In one embodiment, a method includes administering to the subject an antibody that binds to LFA-1 alpha subunit (CD11a) in an amount greater than 1 mg/kg body weight, for example, greater than 1.25 to 1.5, 1.5 to 1.75, 1.75 to 2.0, 2.0 to 2.5, 2.5 to 3.0, 3.0 to 5.0 mg/kg body weight, or greater. In various aspects, the antibody inhibits binding of S6F1 or TS2/4 antibody to LFA-1 alpha subunit; binds to an epitope to which S6F1 or TS2/4 antibody binds; is a humanized form of S6F 1 or TS2/4. In further aspects, the antibody binds an epitope including an LFA-1 alpha subunit β-propeller domain, e.g., located all or in a part of amino acids 1 to 57 of LFA-1 alpha subunit, such as all or a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha as set forth in SEQ ID NO:2. In additional aspects, the antibody is a subsequence of full length antibody containing two variable chains and two constant regions, e.g., an Fab, Fab', (Fab)$_2$, Fv or scFv. In yet additional aspects, the antibody that binds to LFA-1 alpha subunit is a humanized form, e.g., having one or more amino acid substitutions, additions or deletions, provided that said antibody has a binding affinity for LFA-1 alpha subunit or an epitope in LFA-1 alpha subunit within about 1 to 3, 2 to 5, 5 to 10, 10 to 50 or 10 to 100 of the binding affinity of S6F1 or TS2/4.

The invention additionally provides methods of treating a subject having or at risk of having a physiological condition treatable with an antibody that binds to LFA-1 alpha subunit (CD11a). comprising administering to the subject an antibody that binds to LFA-1 alpha subunit in an amount greater than 1 mg/kg body weight. In one embodiment, a method includes administering to the subject an antibody that binds to LFA-1 alpha subunit (CD11a) in an amount greater than 1 mg/kg body weight, for example, greater than 1.25 to 1.5, 1.5 to 1.75, 1.75 to 2.0, 2.0 to 2.5, 2.5 to 3.0, 3.0 to 5.0 mg/kg body weight, or greater. In various aspects, the antibody inhibits binding of S6F1 or TS2/4 antibody to LFA-1 alpha subunit; binds to an epitope to which S6F1 or TS2/4 antibody binds; is a humanized form of S6F1 or TS2/4. In further aspects, the antibody binds an epitope including an LFA-1 alpha subunit β-propeller domain, e.g., located all or in a part of amino acids 1 to 57 of LFA-1 alpha subunit, such as all or a part of amino acids 1 to 5, 5 to 10, 10 to 15, 15 to 20, 20 to 25, 25 to 30, 35 to 40, 40 to 45, 45 to 50, 50 to 55 or 50 LFA-1 alpha subunit as set forth in SEQ ID NO:2. In additional aspects, the antibody is a subsequence of full length antibody containing two variable chains and two constant regions, e.g., an Fab, Fab', (Fab)$_2$, Fv or scFv. In yet additional aspects, the antibody that binds to LFA-1 alpha subunit is a humanized form, e.g., having one or more amino acid substitutions, additions or deletions, provided that said antibody has a binding affinity for LFA-1 alpha subunit or an epitope in LFA-1 alpha subunit within about 1 to 3, 2 to 5, 5 to 10, 10 to 50 or 10 to 100 of the binding affinity of S6F1 or TS2/4.

The invention moreover provides methods treating a subject exposed to HIV or at risk of exposure to HIV. In one embodiment, a method includes administering to the subject an antibody that binds to LFA-1 alpha subunit (CD11a) in an amount greater than 1 mg/kg body weight, for example, greater than 1.25 to 1.5, 1.5 to 1.75, 1.75 to 2.0, 2.0 to 2.5, 2.5 to 3.0, 3.0 to 5.0 mg/kg body weight, or greater. In various aspects, the antibody inhibits binding of S6F1 or TS2/4 antibody to LFA-1 alpha subunit; binds to an epitope to which S6F1 or TS2/4 antibody binds; is a humanized form of S6F1 or TS2/4. In further aspects, the antibody binds an epitope including an LFA-1 alpha subunit β-propeller domain, e.g., located all or in a part of amino acids 1 to 57 of LFA-1 alpha subunit, such as all or a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha as set forth in SEQ ID NO:2. In additional aspects, the antibody is a subsequence of full length antibody containing two variable chains and two constant regions, e.g., an Fab, Fab', (Fab)$_2$, Fv or scFv. In yet additional aspects, the antibody that binds to LFA-1 alpha subunit is a humanized form, e.g., having one or more amino acid substitutions, additions or deletions, provided that said antibody has a binding affinity for LFA-1 alpha subunit or an epitope in LFA-1 alpha subunit within about 1 to 3, 2 to 5, 5 to 10, 10 to 50 or 10 to 100 of the binding affinity of S6F1 or TS2/4. In yet further aspects, the subject is asymptomatic or symptomatic for HIV infection or has not been previously exposed to HIV.

Methods of the invention include administering to a subject, systemically or locally, a single or multiple doses. In various aspects, where the first dose administered is greater than 1 mg/kg body weight, one or more subsequent doses may be in an amount less than 1 mg/kg body weight or in an amount greater than 1 mg/kg body weight.

The invention still further provides compositions, including kits, including the antibodies. In various embodiments, a composition or kit includes 100 mg or more S6F1, TS2/4 antibody, humanized form or subsequence thereof, and a pharmaceutically acceptable carrier, said composition optionally in single or multiple unit dosage forms, e.g., multiple unit dosage forms of 100 mg or more S6F 1, TS2/4 antibody, humanized form or subsequence thereof. In various aspects, a composition or kit includes a composition present in an ampule, vial, bottle or syringe. In additional aspects, a kit includes instructions for administering greater than 1 mg/kg body weight of the composition to the subject, for example, 1.25 to 1.5, 1.5 to 1.75, 1.75 to 2.0, 2.0 to 2.5, 2.5 to 3.0, 3.0 to 5.0 mg/kg-body weight of the composition, or greater, to the subject.

DETAILED DESCRIPTION

The invention is based, at least in part, on LFA-1 alpha subunit antibodies. When administered at particular dose amounts to a subject, an antibody that binds LFA-1 alpha subunit is able to improve the physiological condition of subjects that exhibit one or more symptoms of HIV infection. For example, HIV viral titers decrease in HIV infected subjects treated with LFA-1 alpha subunit antibody (see, Example 2 and FIG. 1). In addition, numbers of CD4+ cells increase in HIV infected subjects treated with LFA-1 alpha subunit antibody (see, Example 2). HIV infected subjects treated with LFA-1 alpha subunit antibody also reported increased energy and an overall improvement in their well being (see Table 2).

Thus, in accordance with the invention, there are provided methods of treating a subject having or at risk of having a physiological condition associated with or caused by decreased CD4+ cell numbers; methods of increasing CD4+ cell numbers in a subject; methods of inhibiting or preventing decreases in CD4+ cell numbers in a subject; and methods of treating a subject exposed to HIV or at risk of exposure to HIV. In one aspect, a method includes administering to a subject an antibody that binds LFA-1 alpha subunit (CD11a) in an amount greater than 1.0 mg/kg body weight.

The LFA-1 alpha subunit is involved in the immune response pathway. Thus, in addition to an LFA-1 alpha subunit binding antibody being useful for treating a physiological condition associated with or caused by decreased CD4+ cell numbers; increasing CD4+ cell numbers; inhibiting or preventing decreases in CD4+ cell numbers; and treating a subject exposed to HIV or at risk of exposure to HIV, other physiological conditions in which LFA-1 participates in can similarly be treated.

Accordingly, in another embodiment, the invention provides methods of treating a subject having or at risk of having a physiological condition treatable with an antibody that binds to LFA-1 alpha subunit (CD11a). In one aspect, a method includes administering to a subject an antibody that binds LFA-1 alpha subunit (CD11a) in an amount greater than 1.0 mg/kg body weight.

An embodiment of the invention includes a medicament and a method of making a medicament, wherein the medicament contains an antibody that binds LFA-1 alpha subunit (CD11a), such as S6F1 or TS2/4, and the medicament is useful in treating a patient or subject having or at risk of having a physiological condition treatable with such antibody, such as HIV infection.

Physiological conditions or disorders in which LFA-1 alpha subunit participates or which respond to altering one or more LFA-1 alpha subunit activities include, for example, immune disorders such as non-Hodgkin's lymphoma, Reiter's syndrome and progressive generalized lymphadenopathy.

Exemplary antibodies that bind LFA-1 alpha subunit are monoclonal antibodies, such as S6F1 (ATCC accession number HB-9579) and TS2/4 (ATCC Accession number HB-244). These antibodies have been previously described (see, e.g., U.S. Pat. No. 5,002,869; Morimoto et al., *Nature* 330:479 (1987); and Sanchez-Madrid et al., *Proc. Natl. Acad. Sci. USA* 79:7489 (1982)).

Exemplary doses or amounts of antibody used in the methods of the invention are greater than 1.0 mg/kg body weight, e.g., 2.0 mg/kg body weight. In additional embodiments, the dose or amount of antibody administered to a subject comprises between about 1.25 to 1.5, 1.5 to 1.75, 1.75 to 2.0, 2.0 to 2.5, 2.5 to 3.0, 3.0 to 5.0 mg/kg body weight, or greater.

The term "antibody" refers to a protein that binds to other molecules (antigens) via heavy and light chain variable domains, $V_H$ and $V_L$, respectively. Antibodies include IgG (for example, $IgG_1$, $IgG_2$, $IgG_3$, and $IgG_4$), IgM, IgA, IgD, IgE, IgD, IgA, IgM and IgE. By way of example, IgG molecules comprise two identical light polypeptide chains of molecular weight approximately 23,000 Daltons, and two identical heavy chains of molecular weight 53,000–70,000. The four chains are joined by disulfide bonds in a "Y" configuration; the light chains bracket the heavy chains starting at the mouth of the "Y" and continuing through the variable region. Light chains are classified as either kappa or lambda (κ, λ). Each heavy chain class may be bound with either a kappa or lambda light chain. In naturally occurring antibodies, light and heavy chains covalently bind to each other, and the "tail" portions of the two heavy chains bind to each other by covalent disulfide linkages. In the heavy chain, the amino acid sequences run from an N-terminus at the forked ends of the Y configuration to the C-terminus at the bottom of each chain. At the N-terminus is a variable region and at the C-terminus is a constant region. Heavy chains are classified in the art as gamma, mu, alpha, delta, or epsilon, (γ, μ, α, δ, ε) with some subclasses among them which determines the "class" of the antibody as IgA, IgD, IgE, IgG, or IgM.

The variable domains of light ($V_L$) and heavy ($V_H$) chains determine antigen specificity and affinity. The antigen binding site is determined by three complimentary determining regions (CDRs) on each of the $V_H$ and $V_L$ chains. Framework regions largely adopt a β-sheet conformation and the CDRs form loops connecting, and in some cases forming part of, the β-sheet structure. Thus, framework regions form a scaffold that position the six CDRs in an orientation by inter-chain, non-covalent interactions, to allow CDRs to non-covalently bind to the antigen epitope. The constant domains of the light chain ($C_L$) and the heavy chain ($C_H1$, $C_H2$ or $C_H3$) confer biological properties such as secretion, transplacental mobility, Fc receptor binding, complement binding, and the like.

The antibodies may be intact immunoglobulin molecules, two full length heavy chains linked by disulfide bonds to two full length light chains, as well as subsequences (i.e., fragments) of immunoglobulin molecules, with our without constant region, that bind to an epitope of an antigen, or subsequences thereof (i.e., fragments) of immunoglobulin molecules, with or without constant region, that bind to an epitope of an antigen. Antibodies may comprise full length heavy and light chain variable domains, $V_H$ and $V_L$, individually or in any combination.

Antibodies include polyclonal and monoclonal antibodies. A "monoclonal antibody" is an antibody obtained from a population of substantially homogeneous antibodies, i.e., the individual antibodies comprising the population are identical except for possible naturally occurring mutations present in minor amounts. Monoclonal antibodies are specific, they are directed against a single determinant (epitope) on the antigenic site whereas polyclonal antibodies typically include antibodies that bind different antigenic determinants (epitopes). In addition to specificity, monoclonal antibodies are advantageous in that they are produced by hybridoma culture and are therefore uncontaminated with other immunoglobulins.

The term "monoclonal" indicates the antibody as being obtained from a substantially homogeneous population of antibodies, and is not to be construed as requiring production of the antibody by any particular method. For example, monoclonal antibodies may be made by the hybridoma method first described by Kohler et al., *Nature* 256:495 (1975). In this process lymphocytes from a mammal injected with antigen are fused with an immortal tumor cell line (e.g., a myeloma cell line), thus producing hybrid cells or "hybridomas." The hybridomas are immortal and capable of producing antibody. Cloning the hybridomas generates single genetic strains each of which produce a single antibody. The antibodies may then be purified with a commercially available protein G affinity resin or by other techniques known in the art (see, for example, *Antibodies: A Laboratory Manual*, Harlow and Lane (eds.), Cold Spring Harbor Laboratory Press, 1988). Suitable techniques include LFA-1 alpha subunit affinity purification, non-denaturing gel purification, HPLC or RP-HPLC, purification on protein A column, or any combination of these techniques.

Alternatively, monoclonal antibodies may be made by recombinant DNA methods, e.g., using oligonucleotide probes capable of binding specifically to genes encoding heavy and light chains of antibodies, subcloned hybridoma cells can be screened and DNA isolated. Once isolated, the DNA may be inserted into expression vectors, transfected into a prokaryotic or eukaryotic host cell, such as *E. coli*, COS cells, Chinese Hamster Ovary (CHO) cells or myeloma cells, (see, e.g., U.S. Pat. No. 4,816,567). Cloning of constant and variable region sequences for the purpose of producing antibodies is described, e.g., in U.S. Pat. No. 5,658,570). DNA encoding antibodies or antibody subsequences may also be derived from antibody phage libraries as described, e.g., in EP 368 684 B1 and U.S. Pat. No. 5,969,108. Several publications (e.g., Clackson et al., *Nature* 352: 624–628 (1991); and Marks, et al., *Bio/Technology* 10:779–783 (1992)) have described producing high affinity human antibodies by chain shuffling, as well as combinatorial infection and in vivo recombination as a strategy for constructing large phage libraries. Such procedures are alternatives to traditional hybridoma techniques for isolation and subsequent cloning of monoclonal antibodies.

The preparation of polyclonal antibodies and their purification also is well known to those skilled in the art (see, e.g., Green, et al. (1992) In: *Immunochemical Protocols*, pages 1–5, Manson, ed., Humana Press; and Coligan, et al. (1994) In: *Current Protocols in Immunology*, Wiley; and Barnes, et al. (1992) In: *Methods in Molecular Biology*, Vol. 10, pages 79–104, Humana Press).

Anti-LFA-1 alpha subunit antibodies include antibodies that inhibit binding of exemplary S6F1 or TS2/4 monoclonal antibody to LFA-1 alpha subunit. In other words, such inhibitory or competing antibodies will compete with S6F1 or TS2/4 antibody for binding to LFA-1 alpha subunit. These antibodies will likely compete with S6F1 or TS2/4 antibody for binding to LFA-1 alpha subunit on an approximately equimolar basis. In other words, in a mixture with a given molar concentration of S6F 1, an equal molar concentration of competitor antibody will decrease binding of S6F1 to LFA-1 alpha subunit by 50%. This is because the competing antibody has a binding affinity for LFA-1 alpha subunit approximately equal to that of S6F 1. Of course, antibodies that are more or less effective in competing with S6F1 or TS2/4 antibody for binding to LFA-1 alpha subunit are included. For example, an antibody that requires a 2–5 fold greater molar concentration to inhibit binding of S6F1 to LFA-1 alpha subunit by 50% (e.g., 1–2.5 uM of antibody is the amount needed to decrease binding of 0.5 uM of S6F1 or TS2/4 antibody to LFA-1 alpha subunit by 50%), or an antibody in which 2–5 fold less molar concentration can inhibit binding of S6F1 to LFA-1 alpha subunit by 50% (e.g., 0.1–0.5 uM of antibody is the amount needed to decrease binding of 1 uM of S6F1 or TS2/4 antibody to LFA-1 alpha subunit by 50%) are also included. Competitive binding studies are known to the skilled artisan and may be used to identify antibodies that inhibit binding of S6F1 or TS2/4 antibody to LFA-1 alpha subunit.

Anti-LFA-1 alpha subunit antibodies also include antibodies that bind to an epitope to which S6F1 or TS2/4 antibody binds, that is, the antibody has the binding specificity of S6F1 or TS2/4.

As used herein, the term "specificity," when used in reference to antibody binding to an antigen, means that the antibody recognizes the same epitope as a comparison antibody. Thus, an antibody having the binding specificity of the antibody denoted as S6F1 recognizes the same epitope as S6F1; an antibody having the binding specificity of the antibody denoted as TS2/4 recognizes the same epitope as TS2/4; and so on and so forth. Consequently, a comparison antibody which recognizes the same epitope as S6F1 or TS2/4 could be readily identified by a simple assay, for example, a competition assay wherein the comparison antibody inhibits the binding of S6F1 or TS2/4, respectively.

As used herein, the term "bind" or "binding," when used in reference to the interaction between antigen and antibody, means that the binding is selective between two molecules. Typically, binding which occurs between an antibody and an antigen can be distinguished from nonspecific binding when the dissociation constant ($K_D$) is less than about $1 \times 10^{-5}$ M or less than about $1 \times 10^{-6}$ M or $1 \times 10^{-7}$ M.

For LFA-1 alpha subunit, S6F1 is believed to bind to an epitope located entirely within or within at least a part of amino acids 1 to 57 of LFA-1 alpha subunit denoted as SEQ ID NO:2 (Genbank accession number NM002209; Corbi, et. al., *J. Exp. Med.* 167(5):1597–1607 (1988); Loftus, et.al., *Genomics* 60 (3), 295–308 (1999)). Typically, epitopes are short amino acid sequences, e.g., at least about five amino acids in length. The epitope to which antibodies useful in the methods of the invention bind may therefore be located entirely within or within a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha subunit denoted as SEQ ID NO:2. Antibodies that bind such regions of LFA-1 alpha subunit are therefore useful in accordance with the invention. (Huang and Springer, *Proc. Natl. Acad. Sci USA* 94:3162–3167 (1997))

LFA-1 beta (β)-propeller domain may contain one or more epitopes to which exemplary antibodies S6F1 or TS2/4 bind (Zang, et. al., *J. Biol. Chem.* 275(29):22202 (2000)). Anti-LFA-1 alpha subunit antibodies therefore also include antibodies that bind to an LFA-1 alpha subunit beta-propeller domain or epitope therein. There are at least three beta-sheet domains located in amino acids 1 to 57 of LFA-1 alpha subunit (Huang and Springer, *Proc. Natl. Acad. Sci. USA* 94:3162–3167 (1997)). The N-terminal portion beta-propeller domain is predicted to contain seven beta-sheets, the first three of which are located in amino acids, 1 to 57 of LFA-1 alpha subunit denoted as SEQ ID NO:2. Therefore, an antibody that binds to an epitope located entirely within or at least within a part of a beta-sheet or beta-propeller domain of LFA-1 alpha subunit is useful in accordance with the invention.

Antibodies that bind a given epitope may be produced by immunizing animals with epitope length peptide sequences. As such, antibodies that bind to all or a part of LFA-1 alpha subunit amino acids 1 to 5, 5 to 10, 10 to 15, 15 to 20, 20 to 25, 25 to 30, 35 to 40, 40 to 45, 45 or to 55 or 50 to 57 as set forth in SEQ ID NO:2, or a beta-sheet or beta-propeller domain of LFA-1 alpha subunit are included.

Antibodies that bind to LFA-1 alpha subunit may be characterized for their epitope specificity. Systematic techniques for identifying the epitopes to which antibodies bind are known in the art and are described, for example, in U.S. Pat. No. 4,708,871. Briefly, a set of overlapping oligopeptides derived from LFA-1 alpha subunit, such as amino acids 1 to 57 or a beta-sheet or beta-propeller domain, or a sequence therein, may be synthesized and bound to a solid phase array of pins, with a unique oligopeptide on each pin. The array of pins may comprise a 96-well microtiter plate, permitting one to assay all 96 oligopeptides simultaneously, e.g., for binding to an anti-LFA-1 alpha subunit antibody. Alternatively, phage display peptide library kits (New England BioLabs) are currently commercially available for epitope mapping. Using these methods, the binding affinity for every possible subset of consecutive amino acids may be determined in order to identify the epitope that a given antibody binds.

Antibodies useful in accordance with the invention include antibodies having the binding affinity for LFA-1 alpha subunit or an epitope in LFA-1 alpha subunit within about 1 to 3, 2 to 5, 5 to 10, 10 to 50 or 10 to 100 of the binding affinity of S6F1 or TS2/4. Such antibodies having a binding affinity for LFA-1 alpha subunit within about 1 to 3, 2 to 5, 5 to 10, 10 to 50 or 10 to 100 of the binding affinity of S6F1 or TS2/4 further include humanized antibodies such as humanized S6F1 or TS2/4, fully human antibodies as well as modified forms and variants thereof as described herein. Techniques for measuring antibody binding affinity are routine and well known to those of ordinary skill in the art.

Thus, in another embodiment, the invention provides methods of treating a subject having or at risk of having a physiological condition associated with or caused by decreased CD4+ cell numbers; methods of increasing CD4+ cell numbers in a subject; methods of inhibiting or preventing decreases in CD4+ cell numbers in a subject; methods of treating a subject having or at risk of having a physiological condition treatable with an antibody that binds to LFA-1 alpha subunit (CD11a); and methods of treating a subject exposed to HIV or at risk of exposure to HIV using antibodies having the same or altered binding affinity for LFA-1 alpha subunit in comparison to S6F1 or TS2/4. In one embodiment, an antibody is humanized, e.g., a humanized form of S6F1 or TS2/4, or has one or more amino acid substitutions, additions or deletions, provided that the antibody has a binding affinity for LFA-1 alpha subunit or an epitope in LFA-1 alpha subunit within about 1 to 3, 2 to 5, 5 to 10, 10 to 50 or 10 to 100 of the binding affinity of S6F1 or TS2/4. In another embodiment, the antibody has a binding affinity for LFA-1 alpha subunit or an epitope in LFA-1 alpha subunit within about 1 to 3, 2 to 5, 5 to 10, 10 to 50 or 10 to 100 of the binding affinity of S6F 1 or TS2/4. In another embodiment, the antibody comprises a fully human antibody having a binding affinity for LFA-1 alpha subunit or an epitope in LFA-1 alpha subunit within about 1 to 3, 2 to 5, 5 to 10, 10 to 50 or 10 to 100 of the binding affinity of S6F1 or TS2/4.

Modified forms of antibodies are included. Modified antibodies include variants having one or more amino acid deletions. An example of a deletion is where one or more amino acids are deleted from the N- or C-terminal end, or internally within the amino acid sequence. Thus, antibodies include intact or full length monoclonal and polyclonal antibodies, as well as biologically active subsequences thereof, i.e., immunoglobulin fragments that retain all or at least a part of the activity of the parent or reference antibody, (e.g., a native antibody having two full length heavy and variable chain sequences). Exemplary activities include, for example, the ability to retain at least a part of the binding specificity or binding affinity for the antigen to which the parent (unmodified or full length) antibody binds. Thus, in the case of an antibody that binds to LFA-1 alpha subunit, for example, a S6F1 subsequence, the subsequence will retain at least partial binding affinity or specificity for LFA-1 alpha subunit as the parent S6F1 antibody.

As used herein, the term "subsequence" or "fragment" means a portion of the full length molecule. For example, a subsequence of an antibody is one which is one or more amino acids less in length than the reference, e.g., full length, polypeptide (e.g. one or more internal or terminal amino acid deletions from either amino or carboxy-termini). Subsequences therefore can be any length up to the full length molecule.

Specific examples of antibody subsequences include, for example, Fab, Fab', (Fab')$_2$, Fv, or single chain antibody (SCA) fragment (e.g., scFv). Subsequences include portions that retain at least part of a function or activity of full length sequence. For example, an antibody subsequence will retain the ability to selectively bind to an antigen even though the binding affinity of the subsequence may be greater or less than the binding affinity of the full length antibody. Subsequences can comprise a portion of S6F1 or TS2/4, for example.

Pepsin or papain digestion of whole antibodies can be used to generate antibody subsequences. In particular, an Fab fragment consists of a monovalent antigen-binding subsequence of an antibody molecule, and can be produced by digestion of a whole antibody molecule with the enzyme papain, to yield a fragment consisting of an intact light chain and a portion of a heavy chain. An (Fab')$_2$ subsequence of an antibody can be obtained by treating a whole antibody molecule with the enzyme pepsin, without subsequent reduction. An Fab' fragment of an antibody molecule can be obtained from (Fab')$_2$ by reduction with a thiol reducing agent, which yields a molecule consisting of an intact light chain and a portion of a heavy chain. Two Fab' subsequences are obtained per antibody molecule treated in this manner.

An Fv fragment is a fragment containing the variable region of a light chain $V_L$ and the variable region of a heavy chain $V_H$ expressed as two chains. The association may be non-covalent or may be covalent, such as a chemical cross-linking agent or an intermolecular disulfide bond (Inbar et al., *Proc. Natl. Acad. Sci. USA* 69:2659 (1972); Sandhu *Crit. Rev. Biotech.* 12:437 1992).

A single chain antibody ("SCA") is a genetically engineered or enzymatically digested antibody containing the variable region of a light chain $V_L$ and the variable region of a heavy chain, optionally linked by a flexible linker, such as a polypeptide sequence, in either $V_L$-linker-$V_H$ orientation or in $V_H$-linker-$V_L$ orientation. Alternatively, a single chain Fv fragment can be produced by linking two variable domains via a disulfide linkage between two cysteine residues. Methods for producing scFv antibodies are described, for example, by Whitlow et al., (1991) In: *Methods: A Companion to Methods in Enzymology* 2:97; U.S. Pat. Nos. 4,946,778 5,892,019; and Pack et al., (1993) *Bio/Technology* 11:1271.

Other methods of producing antibody subsequences, such as separation of heavy chains to form monovalent light-heavy chain fragments, further cleavage of fragments, or other enzymatic, chemical, or genetic techniques may also be used, provided that the subsequences retain at least a part of the antigen binding specificity or affinity as the intact reference antibody.

Modified antibodies further include variants having amino acid substitutions, so long as the substituted variant retains at least a part of an activity of the unsubstituted reference antibody. Exemplary amino acid substitutions include conservative amino acid substitutions. The term "conservative substitution" means the replacement of one amino acid by a biologically or chemically similar residue. Biologically similar means that the substitution is compatible with biological activity, e.g., for a humanized antibody, antigen binding. Particular examples of conservative substitutions include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Another particular example of such a variant is a non-human antibody that has been substituted with one or more human amino acids. Another example of such a variant is a human antibody acceptor that has been substituted with one or more non-human donor amino acids (e.g., CDRs). Such "humanized" antibodies therefore contain either 1) a sequence based upon or derived from a non-human immunoglobulin, in which one or more non-human amino acids have been substituted with one or more human residues; or 2) a human acceptor antibody sequence in which one or more non-human amino acids have been "grafted" into the human acceptor. Another example of such a variant is a non-human antibody that has been substituted with an amino acid that decreases immunogenicity in a human. Humanized antibodies therefore are generally either 1) less immunogenic in humans following substitution; or 2) contain at least one amino acid residue typically found in human antibodies. Such antibodies also include full length immunoglobulin molecules or subsequences thereof (such as Fv, scFv, Fab, Fab', F(ab')$_2$ or other antigen-binding subsequences), which retain at least a part of the antigen binding specificity or affinity of the reference antibody.

Any non-human antibody producing organism, such as mouse, rat, rabbit, pig, horse, goat, guinea pig, or non-human primate (e.g., ape, chimpanzee, macaque, orangutan, etc.) or other animal may be used as a CDR donor for a human acceptor, or as an acceptor of human amino acids to produce humanized antibody. For example, amino acid residues in one or more of variable framework region (FR) residues of a complementarity-determining region (CDR; the framework residues flank the hypervariable regions) of a non-human antibody may be substituted with one or more human amino acid residues. Thus, a human amino acid substitution for a non-human amino acid typically maintains the CDR in a conformation that retains all or at least of part of antigen binding affinity or specificity while simultaneously decreasing immunogenicity in humans. In a particular example, the humanized antibody includes all of or at least one variable domain, in which all or a part of one or more of the CDR regions correspond to those of a non-human immunoglobulin and all or a part of the FR regions are those of a human immunoglobulin sequence. The humanized antibody may also include at least a portion of an immunoglobulin constant region (Fc) of a human immunoglobulin.

Humanized antibodies may be obtained using a variety of methods known in the art such as: (a) grafting the non-human variable domains onto human constant regions to generate chimeric antibodies; (b) grafting at least a part of one or more of the non-human complementarity determining regions (CDRs) into a human framework and constant regions; or (c) transplanting the entire non-human variable domains, but "cloaking" them with a human-like section by replacement of surface residues. Such methods are described, for example, in Morrison et al., *Proc. Natl. Acad. Sci.* 81:6851 (1984); Morrison et al., *Adv. Immunol.* 44:65 (1988); Verhoeyen et al., *Science* 239: 1534(1988); Padlan, *Molec. Immun.* 28:489 (1991); Padlan, *Molec. Immun.* 31:169 (1994), and U.S. Pat. Nos. 5,585,089; 5,693,761; and 5,693,762.

Humanized antibodies may comprise residues which are found neither in the recipient antibody nor in the imported CDR or framework sequences. For example, a consensus human immunoglobulin sequence may be used to select particular amino acids for substitution of non-human amino acids due to their structural similarity with the non-human residue. A "consensus" antibody sequence is a sequence having the most frequently occurring amino acid residues at particular positions in an antibody or an antibody region after surveying a plurality of human antibody sequences. As an example, human variable region domain sequences are described in Kabat (*Sequences of Proteins of Immunological Interest*. 4$^{th}$ Ed. U.S. Department of Health and Human Services. Public Health Service (1987)). Sequences that are completely determined in the framework regions, 1–23, 35–49, and 57–88 in the light chains, and in the framework regions, 1–30, 36–49, and 66–94, in the heavy chains, are surveyed. The most frequently occurring residue at a given position is selected as the residue for the consensus sequence. Human consensus sequences may therefore be identified by surveying amino acid residues at each position of a plurality of antibodies; the most frequently occurring amino acid at a given position is a part of the consensus.

The published consensus sequence of human $V_H$ subgroup III, based on a survey of 22 known human $V_H$ III sequences, and the published consensus sequence of human $V_L$ kappa-chain subgroup I, based on a survey of 30 known human kappa I sequences may be used for human antibody (Padlan, *Mol. Immunol.* 31:169 (1994); Padlan, *Mol. Immunol.* 28:489 (1991)). Genes for the two classes of human light chains and the five classes of human heavy chains have been cloned, and thus, constant regions of human origin are available from publicly available databases. For further details, see Jones et al., *Nature,* 321:522 (1986); Reichmann et al., *Nature,* 332:323 (1988); and Presta, *Curr. Op. Struct. Biol.,* 2:593(1992).

Modified antibodies further include variants having one or more amino acid additions or insertions. An example of an addition is where one or more amino acids are added to the N- or C-terminal end of a humanized antibody. An example of an insertion is where an amino acid is inserted into the sequence. A particular example is where a different immunoglobulin sequence has been added to another immunoglobulin sequence. Antibodies therefore include "chimeric" antibodies in which all or a portion of the heavy or light chain is identical to or homologous with corresponding sequences in antibodies derived from a particular species or belonging to a particular antibody class or subclass, while the remainder of the chain(s) is identical to or homologous with corresponding sequences in antibodies derived from another species or belonging to another antibody class or subclass, as well as fragments of such antibodies (U.S. Pat. No. 4,816,567; Morrison, et al., *Proc. Natl. Acad. Sci. USA,* 81: 6851–5 (1984)). Thus, a particular example of such a variant is a multi-specific antibody. The term "multispecific" means an antibody that binds to two or more different antigenic epitopes. A "multispecific" antibody contains two or more variable region sequences that bind to different epitopes. For example, a bi-specific antibody includes a first variable chain that binds a first epitope and a second variable chain that binds to a different second epitope.

Additions include heterologous peptide sequences other than immmunoglobulin sequences, a heterologous peptide sequence, to form a fusion or chimeric antibody. The heterologous sequence may contain an activity distinct from the antibody portion of the chimera. Thus, another particular example of such a variant is a multi-functional antibody. The term "multifunctional" means that the composition referred to has two or more activities or functions (e.g., antigen binding, enzyme activity, ligand or receptor binding, toxin, etc.). For example, an antibody that binds to a particular antigen which also has an attached polypeptide with enzyme activity (e.g., luciferase, acetyltransferase, galactosidase, peroxidase, etc.) is an example of a bifunctional antibody which has a binding function and a second function.

Candidate functions for multifunctional antibodies in addition to enzyme activity include, for example, detectable moieties such as radioisotopes and amino acid sequences (e.g., $^{35}S$, $^{131}I$, T7, immunoglobulin or polyhistidine tags, toxins (e.g., ricin, cholera, pertussis), cell surface proteins such as receptors, ligands (substrates, agonists and antagonists), adhesion proteins (e.g., streptavidin, avidin, lectins), growth factors, differentiative factors and chemotactic factors.

Additions are not restricted to amino acid sequences. Thus, a functional domain can be added that contains any of a variety of different types of small or large functional moieties. Such moieties include nucleic acid, peptide, carbohydrate, lipid or small organic compounds, such as a drug (e.g., a chemothrerapeutic drug such as vincristine, methotrexate, etc.), detectable label (fluorophores, chromophores, radionuclides, etc.).

Variants having amino acid additions, deletions and substitutions can be produced by expressing nucleic acid encoding the particular variant in a cell, e.g., insect, or mammalian cells, and isolating the variant antibody from the cell or culture medium. For example, variable region genes can be obtained by standard DNA cloning procedures from cells that produce the desired antibody. Of course, genes may be chemically synthesized using any of several commercially available automated synthesizers (e.g., ABI Model 403A). In addition, DNA sequences encoding heavy and light chains can be obtained through the services of commercial DNA synthesis vendors.

Alternatively, once a DNA sequence encoding the antibody is obtained, e.g., by screening of a genomic library for a specific functionally rearranged variable region or an expression library (e.g., mRNA) with the use of an appropriate probe, amino acid variations may be introduced into the DNA sequence using polymerase chain reaction (PCR) based mutagenesis. For example, the genetic sequence corresponding to variable or constant regions of the antibody may be isolated and appropriate nucleotides modified or deleted to provide variant antibodies in accordance with the invention. More particularly, single or multiple nucleotide mutations may be introduced into DNA fragments to encode different amino acids at positions within a heavy or light chain variable region or constant region using PCR based mutagenesis. PCR based methods of adding amino acid residues to an antibody or fusing a an amino acid sequence to an antibody in order to produce chimeric or fusion antibodies are also known in the art.

Multi-specific and -functional antibodies can be produced through chemical crosslinking of the selected molecules (which have been produced by synthetic means or by expression of nucleic acid that encode the polypeptides) or through recombinant DNA technology combined with in vitro, or cellular expression of the polypeptide, fusion of hybridomas that produce antibodies with different epitopic specificities, or expression of multiple nucleic acid encoding antibody variable chains with different epitopic specificities in a single cell.

The genetic material obtained encoding all or a part of the immunoglobulin is assembled or inserted into a vector for additional manipulation or for subsequent incorporation into a recipient cell and expression. Such vectors may be selected from plasmids, phages and viruses. Vectors may optionally include a selection marker, appropriate restriction sites to facilitate cloning of the gene and the ability to enter or replicate in eukaryotic or prokaryotic cells. Introduction of the plasmid into the host cell can be accomplished by various techniques including transfection (e.g., electrophoresis and electroporation), protoplast fusion, calcium phosphate precipitation, cell fusion with enveloped DNA, microinjection, and infection with virus. See, Ridgway, A. A. G. "*Mammalian Expression Vectors*" Chapter 24.2, pp. 470–472 Vectors, Rodriguez and Denhardt, Eds. (Butterworths, Boston, Mass. 1988). The introduction of gene constructs into plasmid vectors for cloning and manipulation and into expression vectors for cell expression can be accomplished by a variety of methods known in the art.

Recipient cell lines for antibody expression include lymphoid cells such as a myeloma (or hybridoma). Myelomas can synthesize, assemble, and secrete immunoglobulins encoded by transfected genes, and they post-translationally modify the protein. A particular recipient cell is the Sp2/0 myeloma which normally does not produce endogenous immunoglobulin. When transfected, the cell will produce only immunoglobulin encoded by the transfected gene. Transfected myelomas can be grown in culture and isolated from the culture medium or grown in the peritoneum of mice where secreted immunoglobulin can be recovered from ascites fluid. Other lymphoid cells, such as B lymphocytes, also can be used as recipient cells.

Modifications also include derivatized sequences. For example, amino acids in which free amino groups form amine hydrochlorides, p-toluene sulfonyl groups, cabrobenzoxy groups; the free carboxy groups from salts, methyl and ethyl esters; free hydroxl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Also included are modifications that confer covalent bonding, for example, a disulfide linkage between two cysteine residues thereby producing a cyclic polypeptide.

Further provided are fully human antibodies which have a binding affinity for LFA-1 alpha subunit or an epitope in LFA-1 alpha subunit within about 1 to 3, 2 to 5, 5 to 10, 10 to 50 or 10 to 100 of the binding affinity of S6F 1 or TS2/4.

As used herein, the term "human" or "fully human," when used in reference to an antibody, means that the antibody is entirely human. Human antibodies may be generated using animals (e.g., mice) that are incapable of endogenous immunoglobulin production (see e.g., U.S. Pat. Nos. 6,075,181; 5,939,598; 5,591,669; and 5,589,369). For example, homozygous deletion of the antibody heavy-chain joining region in chimeric and germ-line mutant mice results in complete inhibition of endogenous antibody production. Transfer of a human immunoglobulin gene array into such a germ line mutant mice will result in the production of human antibodies when the animals are exposed to antigen.

Alternatively, human transchromosomic (Tc) mice, which contain kappa or lambda human IgG chains in their chromosomes (Tomizuka et al., *Proc. Natl. Acad. Sci. USA* 97:722 (2000) and Tomizuka, et al., *Nat Genet* 16:133 (1997)), may be immunized with antigen or an epitope. Monoclonal antibodies were then prepared from the animals showing highest antibody titers using the method of Kohler, *Nature* 256:495 (1975). The resulting hybridomas are plated and assayed for the production of heavy or kappa chains and then for antibody production. Cells may then be cloned by limiting dilution and rescreened for antibody production.

Methods of the invention include combination therapies. For example, a method of treating a subject having or at risk of having HIV may optionally include additional drugs or therapies to treat HIV. Subjects undergoing combination therapies may be administered or treated with the drug or therapy prior to, contemporaneously with or following treatment with an antibody that binds LFA-1 alpha subunit.

Exemplary drugs or therapies for use in combination with the methods and compositions of the invention include anti-virals, such as protease inhibitors; anti-immune cell stimulating or immune cell inhibiting drugs, as appropriate, such as cytokines, chemokines, interleukins, interferons and molecules that bind them such as their receptors; anti-inflammatories such as steroidal and non-steroidal drugs.

Specific examples of antivirals, which inhibit viral protease, reverse transcriptase or integrase include, for example, viral fusion inhibitors, e.g., T20 and T20 analogues (Trimeris, Inc.); entry inhibitors; integrase inhibitors; protease inhibitors (e.g., saquinavir, ritonavir, indinavir, nelfinavir, amprenavir); a nucleoside reverse transcriptase inhibitor (e.g., zidovudine (AZT), stavudine (d4T), larnivudine (3TC), didanosine (DDI), zalcitabine (ddC), abacavir); a non-nucleoside reverse transcriptase inhibitor (e.g., nevirapine, delavirdine, efavirenz); viral maturation into infectious virus (e.g., "zinc finger injectors," a class of inhibitors that inhibit proper viral α nuclear capsid protein assembly thereby preventing formation of infectious viral particles); and mixtures thereof.

Specific examples of steroidal anti-inflammatory agents include glucocorticoids. Non-limiting illustrative examples of steroidal anti-inflammatory agents include, for example, flunisolide, triamcinoline, triamcinoline acetonide, beclomethasone diproprionate, betamethasone diproprionate, hydrocortisone, cortisone, dexamethasone, budesonide, prednisone, methyl prednisolone, prednisolone, esters of any of these compounds and combinations thereof. Nonlimiting illustrative specific examples of non-steroidal anti-inflammatory agents (NSAIDs) include, for example, pyrazolones, such as phenylbutazone, oxyphenbutazone, dipyrone and isopyrin, and xicams, which include piroxicam and miloxicam; the salicylates, e.g., acetylsalicylate (aspirin); propionic acids, e.g., ibuprofen and naproxen; anthranilic acids, e.g., meclofenamic acid; phenylacetic acids, e.g., acetaminophen; aminonicotinic acids, e.g., flunixin; and indolines, e.g., indomethacin. Other non-limiting examples of anti-inflammatory agents include Thalidomide (made by Celgene).

A "subject" is a living animal such as a mammal. Exemplary subjects include humans and non-human primates (e.g., gorillas, chimpanzees, orangutans, macaques, gibbons). Non-human mammals include, for example, dogs, cats, pigs, cows, sheep, goats, horses, rats, rabbits and mice. Human subjects include adults, and children, for example, neonates and newborns. Subjects include disease model animals (e.g., such as HIV or SIV infected non-human primates).

Candidate subjects suitable for treatment in the methods of the invention include, for example, subjects who have deficient CD4+ cell numbers or are immunosuppressed due to disease or therapy (e.g., anti-cell proliferative therapy such as chemotherapy or an immunosuppressive therapy) or are at risk of decreases in CD4+ cell numbers. Candidate subjects suitable for treatment also include subjects in which it is desired to increase numbers of CD4+ cells, such as immunocompromised subjects or those at risk of becoming immunocompromised. Such subjects therefore include any disease or treatment that results in decreased numbers of CD4+ cells, or any disease or treatment in which increasing the CD4+ cell numbers would improve the subjects condition.

Candidate subjects suitable for treatment in the methods of the invention include subjects who have been exposed to HIV, whether they are symptomatic or asymptomatic, or whether they produce detectable antibody HIV protein or not. Hence, candidate subjects may or may not have been exposed to HIV, have one or more symptoms of HIV, or may be predisposed or at risk of the disease, such as, for example, sexual contact with an HIV+ or probable HIV+ individual, but who has yet to produce detectable anti-HIV protein antibody or one or more symptoms of HIV.

Successful treatment will result in an improvement in the subjects condition or inhibition or reversal of one or more of the physiological, biochemical or cellular manifestations or characteristics of the disease. Successful treatment includes a reduction in the severity or frequency of symptoms, an improvement in the subjects subjective feeling, such as increased energy, appetite, psychological well being, etc. Of course, stabilization of a disease in respect to one or more of the physiological, biochemical or cellular manifestations in which the disease is known to progressively worsen is also considered a successful treatment.

For example, HIV infected subjects typically suffer a gradual increase in viral titer and decline in CD4+ cell numbers as the disease progresses. Thus, inhibiting an increase or decreasing viral titer, or inhibiting decreases or increasing the number of CD4+ cells in the subject is considered an improvement in the subjects' condition. Accordingly, the term "therapeutically effective" means an amount, dose regimen or treatment protocol or combination thereof that achieves a successful treatment effect, such as an amount of an anti-LFA-1 alpha subunit antibody that increases CD4+ cell numbers or prevents or inhibits decreases in CD4+ cell numbers, i.e., stabilizes CD4+ cell numbers; or decreases or stabilizing HIV titer or HIV protein levels; improving energy levels or subjective well being, decreasing the number or severity of opportunistic infection or disease associated with HIV infection, etc.

An improvement may be relatively short in duration, e.g., several hours, days or weeks, or extend over a longer period of time, e.g., months or years. The improvement need not be a complete ablation of any or all symptoms of the disorder. For example, reducing but not completely ablating the symptoms associated with HIV is an improvement. Thus, a satisfactory clinical endpoint and, therefore, successful treatment is achieved when there is an incremental improvement in the subjects condition or a partial reduction in one or more associated symptoms, over a short or long time period.

An effective dosage will generally be greater than 1.0 mg/kg. The skilled artisan will recognize that dosages may vary according to various factors such as the disease treated and whether the disease is in an early or later stage, age, sex, physical condition/health, and weight of the subject, for example. The dosage regimen may therefore be adjusted to provide the optimum therapeutic response, optionally minimizing deleterious side effects. For example, several divided doses may be administered daily, on alternating days (e.g., every other day, third day, forth day, fifth day, etc.), weekly, monthly. The dose may be proportionally increased or reduced as indicated by the status of the disease being treated or the side effects of the treatment. For example, a first dose of greater than 1.0 mg/kg antibody that binds LFA-1 alpha subunit may be subsequently followed by one or more reduced dosages, such as 1.0 mg/kg antibody or less (e.g., 0.75, 0.5, 0.25, 0.1, or less mg/kg). A first dose greater than 1.0 mg/kg antibody that binds LFA-1 alpha subunit may be subsequently followed by one or more increased dosages, such as 1.0 mg/kg antibody or greater (e.g., 1.25, 1.5, 1.75, 2.0, 2.5, 3.0, or greater mg/kg).

Methods of the invention also include prophylactic or preventative treatment. In the prophylactic treatment methods of the invention, the amount administered is capable of inhibiting or preventing decreases in CD4+ cell numbers. In the case of HIV, transmission, which occurs by at least three known routes: sexual contact, blood (or blood product) transfusion and via the placenta, is inhibited or prevented. Transmission may be inhibited by either administering to a non-infected individual to decrease their probability of HIV infection from an HIV-infected individual, or by administering to an HIV-infected individual to decrease the probability of HIV infection of another.

Candidate subjects for prophylactic or preventative treatment methods include those at risk of exposure to or development of the condition. For HIV, candidate subjects therefore include any person who may be exposed to bodily fluids or secretions of an HIV infected subject. Particular examples include homo- or hetero-sexual partners; persons that are exposed or are at risk of exposure to hypodermic needles, such as intravenous drug users or hospital, clinic or laboratory personnel; subjects who receive blood product supplements such as hemophiliacs, or transfusions, such as patients that undergo surgery or who are seriously injured; organ or tissue transplant recipients. Since contact with HIV does not necessarily result in symptomatic infection, as determined by seroconversion, all humans are potentially at risk and, therefore, should be considered for prophylactic treatment using a method of the invention.

The antibodies and combinations thereof used in accordance with the methods of the invention, including subsequences, modified forms and variants, can be incorporated into pharmaceutical compositions or formulations. Such pharmaceutical compositions are useful for administration to a subject in vivo or ex vivo, and for providing therapy for a physiological disorder or condition treatable as set forth herein.

The antibodies can be administered in a conventional dosage form prepared by combining the antibody with a conventional pharmaceutically acceptable carrier or diluent according to known techniques. The form and character of the pharmaceutically acceptable carrier or diluent is dictated by the amount of active ingredient with which it is to be combined; the route of administration and other well-known variables.

Pharmaceutical compositions include "pharmaceutically acceptable" and "physiologically acceptable" carriers, diluents or excipients. As used herein the term "pharmaceutically acceptable" and "physiologically acceptable" includes solvents (aqueous or non-aqueous), detergents, solutions, emulsions, dispersion media, coatings, isotonic and absorption promoting or delaying agents, compatible with pharmaceutical administration and chemically compatible with the other components of the formulation, such as an antibody that binds LFA-1 alpha subunit. Thus, except insofar as any conventional media or agent destroys activity of the active compound, use of any such substance in the compositions is included.

Such formulations can be contained in a tablet (coated or uncoated), capsule (hard or soft), microbead, emulsion, powder, granule, crystal, suspension, syrup or elixir. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes.

Pharmaceutical compositions for parenteral, intradermal, or subcutaneous administration can include a sterile diluent, such as water, saline solution, fixed oils, polyethylene glycols, glycerine, propylene glycol or other synthetic solvents. These preparations may contain one or more preservatives to prevent the growth of microorganisms; antibacterial agents such as benzyl alcohol or methyl parabens; antioxidants such as ascorbic acid or sodium bisulfite; chelating agents such as ethylenediaminctetraacetic acid; buffers such as acetates, citrates or phosphates and agents for the adjustment of tonicity such as sodium chloride or dextrose are but a few specific examples.

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and liquid polyetheylene glycol, and the like), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. In many cases, isotonic agents, for example, sugars, polyalcohols such as manitol, sorbitol, sodium chloride are included in the composition. Including an agent which delays absorption, for example, aluminum monostearate and gelatin can prolonged absorption of injectable compositions.

Sterile injectable solutions can be prepared by incorporating the active compound in the required amount in an appropriate solvent with one or a combination of above ingredients followed by filtered sterilization. Generally, dispersions are prepared by incorporating the active compound into a sterile vehicle containing a basic dispersion medium and other ingredients from those above.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives; for transdermal administration, the active compounds are formulated into ointments, salves, gels, or creams as generally known in the art.

Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known to those skilled in the art, for example, as described in U.S. Pat. No. 4,522,811.

Antibodies can be chemically modified by covalent conjugation to a polymer to increase their circulating half-life, for example. Particular polymers, and methods to attach them to peptides, are described in U.S. Pat. Nos. 4,766,106; 4,179,337; 4,495,285; and 4,609,546. Examples of polymers are polyoxyethylated polyols and polyethylene glycol (PEG).

Additional pharmaceutical formulations and delivery systems are known in the art and are applicable in the methods and compositions of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253–315)

The invention further provides kits comprising one or more antibody compositions of the invention, including pharmaceutical formulations, packaged into suitable packaging material. In one embodiment, a kit includes an antibody that binds to LFA-1 alpha subunit and instructions for practicing a method of the invention. In additional embodiments, a kit includes a label or packaging insert including instructions for treating a subject in vivo, or ex vivo. In yet additional embodiments, a kit includes a label or packaging insert including instructions for treating a subject having or at risk of having HIV with an LFA-1 alpha subunit binding antibody.

As used herein, the term "packaging material" refers to a physical structure housing the components of the kit. The packaging material can maintain the components sterilely, and can be made of material commonly used for such purposes (e.g., paper, corrugated fiber, glass, plastic, foil, ampoules, etc.). The label or packaging insert can include appropriate written instructions, e.g., practicing a method of the invention, e.g., treating HIV. Kits of the invention therefore can additionally include instructions for using the kit components in a method of the invention.

Instructions can include instructions for practicing any of the methods of the invention. Thus, invention pharmaceutical compositions can be included in a container, pack, or dispenser together with instructions for administration to a subject. Instructions may additionally include indications of a satisfactory clinical endpoint or any adverse side effects that may occur, or additional information required by the Food and Drug Administration for use on a human subject.

The instructions may be on "printed matter," e.g., on paper or cardboard within the kit, on a label affixed to the kit or packaging material, or attached to a vial or tube containing a component of the kit. Instructions may comprise a voice recording or video tape and can additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a buffering agent, a preservative, or a protein/nucleic acid stabilizing agent. The kit can also include control components for assaying for activity, e.g., a control sample or a standard. Each component of the kit can be enclosed within an individual container or in a mixture and all of the various containers can be within single or multiple packages.

The antibodies, combination compositions and pharmaceutical formulations thereof can be packaged into a dosage unit form for ease of administration and uniformity of dosage. Such dosages may be included, in single or in multiple dosages, within the kits of the invention for administration in accordance with a method of the invention. "Dosage unit form" as used herein refers to physically discrete units suited as unitary dosages for the subject to be treated; each unit containing a predetermined quantity of active compound calculated to produce the desired therapeutic effect in association with the pharmaceutical carrier or excipient. Dosage forms provided by the invention include, for example, 50–75 mg, 75–100 mg, 100–125 mg, 125–150 mg, 150–175 mg, 175–200 mg or more antibody that binds LFA-1 alpha subunit. Thus, a kit of the invention may include, for example, a single 100 mg dose or multiple 100 mg doses.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to an "LFA-1 alpha subunit antibody" includes a plurality of such antibodies and reference to "an activity" or "function" can include reference to one or more activities or functions, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes human clinical trial design for studying the effect of an exemplary monoclonal antibody, S6F 1, that binds to LFA-1 alpha subunit β-propeller domain.

Purified whole mouse monoclonal $IgG_1$ S6F1 antibody produced by hybridoma technology using an S6F1 producing cell line, HB-9576, obtained from the American Type Culture Collection (Manassas, Va.). The antibody was formulated at a concentration of 1.0 mg/mL in 5 mM sodium phosphate, 1.7 mM potassium phosphate, 154 mM sodium chloride, 5% maltose, pH 7.4. The antibody is produced by the fermentation and expansion of the hybridoma cell line to produce adequate product for harvest (unprocessed bulk). The harvested antibody was processed and purified using a series of purification and concentration steps designed to provide a high-purity antibody with no contaminating materials, which was free of virus or other adventitious agents. The bulk substance was then diafiltered into phosphate-buffered saline and sterile filtered (purified bulk). The purified bulk was then filtered and filled under sterile conditions. The product was filled based on weight using a density of 1 mg/mL and stored at 2–8° C.

A Phase I single-center, open-label, single-dose study to evaluate four escalating doses of the antibody (0.05, 0.1, 0.2, and 0.4 mg/kg body weight) administered by intravenous infusion was designed to determine safety, tolerability, pharmacokinetics, pharmacodynamics, and activity in adults with HIV infection. Eligible patients with plasma HIV RNA concentrations >20,000 copies/mL, CD4+ T-cell counts 200–500 cells/$mm^3$ were sequentially enrolled. Antibody was administered either alone or in conjunction with standard anti-HIV therapy on day 0 by slow IV infusion (0.5 mg protein/min). Hematologic, biochemical, and clinical adverse events were assessed at predetermined times after administration of S6F1 antibody. Preliminary efficacy assessments consisted of change from baseline in HIV RNA concentration, and CD4+ and CD8+ T-cell counts. Parameters were analyzed with summary descriptive statistics.

A Phase Ib/II, single-center, outpatient, open-label, dose-escalating study was designed to evaluate three doses (0.3, 1.0, and 2.0 mg/kg) of S6F1 antibody in twelve HIV-1 infected patients (4 subjects/dose group). The study had two parts: Part 1 evaluated the safety of a single infusion on day 1 by slow IV infusion (1.0 mg protein/min); and Part 2 evaluated repeated infusions given weekly for three doses in the same patients on days 8, 15, and 22 such that patients in part 2 received a total of 4 weekly doses. Eligible patients had viral loads ≧10,000 copies/mL, CD4+ T-cell counts of 200–500 cells/mm$^3$, and a Karnofsky rating of at least 70. Patients were either treatment naïve or were clinically stable on a fixed antiviral regimen for at least eight weeks and agreed to remain on the fixed regimen during the study period. Preliminary analysis of the effect of S6F1 antibody on viral load, CD4+ T-cell count, CD8+ T-cell count, pharmacokinetic parameters and immunogenicity were assessed at predetermined times during the study. Parameters were analyzed with summary descriptive statistics.

Example 2

This example describes the results of the human clinical trials using an exemplary monoclonal antibody, S6F1, that binds to LFA-1 alpha subunit β-propeller domain, to treat HIV.

In the Phase I clinical trial four escalating doses of S6F1 antibody (0.05, 0.1, 0.2, and 0.4 mg/kg body weight) administered by intravenous infusion determined safety, tolerability, pharmacokinetics, pharmacodynamics, and activity in adults with HIV-1 infection. Thirteen men (plasma HIV RNA concentrations >20,000 copies/mL, CD4+ T-cell counts 200–500 cells/mm$^3$) treated with S6F1 antibody were sequentially enrolled in 2 dose groups: 0.05 mg/kg (n=6) and 0.1 mg/kg (n=7). Study enrollment was suspended after the 13 patients had completed treatment in order to review the pharmacokinetic and pharmacodynamic laboratory assays and the data from the first two cohorts. The sensitivity of these assays was inadequate to detect S6F1 antibody in the bloodstream of study patients at these low doses and it was necessary to redesign the assays.

Hematolgic, biochemical, and adverse effects on the 13 patients completing the 0.05 mg/kg and 0.1 mg/kg doses were analyzed. Assessments included the change from baseline. The mean baseline values for HIV-1 RNA, CD4+, and CD8+ T-cell numbers are shown in Table 1.

TABLE 1

Mean Baseline Values

| Dose | HIV (×1000) by PCR | CD4 (cells/mm$^3$) | CD8 (cells/mm$^3$) |
|---|---|---|---|
| 0.05 mg/kg | 185.8 | 229.3 | 1205.3 |
| 0.1 mg/kg | 149.9 | 340.5 | 1117.2 |

In the 0.05 mg/kg dose group, HIV-1 RNA concentration on day 56 was 0.363 log above baseline. The mean CD4+ T-cell count was 15 cells/mm$^3$ below baseline on day 56. Mean CD8+ T-cell count fluctuated, and was 153.6 cells/mm$^3$ below baseline on day 56.

In the 0.1 mg/kg dose group, HIV-1 RNA concentration was 0.229 log below baseline on day 56. Mean CD4+ T-cell count, on day 56, was 70.1 cells/mm$^3$ above baseline. Mean CD8+ T-cell count fluctuated but increased from day 28 until end of study when the CD8+ T cell count was 107.4 cells/mm$^3$ above baseline.

Because of the relatively small number of patients and the low doses evaluated, no conclusions regarding an effect of either dose upon the efficacy parameters can be made. However, patients who received the 0.1 mg/kg dose did have a decrease from baseline in HIV-1 RNA and an increase in CD4+ T-cell numbers at several time points through study day 56 suggesting that S6F1 antibody may reduce lysis of CD4+ T cells thereby reducing HIV-1 viral load.

The overall number of adverse effects was small. Thirteen subjects reported 31 adverse events. The most common adverse event was rash, which occurred in 5 (39%) of subjects. All adverse events were considered mild (97%) to moderate (3%). No adverse events were considered by the investigator to be related to study drug.

The Phase Ib/II, single-center, outpatient, open-label, dose-escalating study was designed to evaluate three doses of S6F1 antibody, 0.3, 1.0, and 2.0 mg/kg, in patients with HIV-1 infection as described in Example 1. A total of 13 patients were enrolled. Two patients received a single infusion of 2.0 mg/kg and 11 patients received 4 weekly infusions (0.3 mg/kg [n=4], 1.0 mg/kg [n=4], and 2.0 mg/kg [n=3]$_j$. Analysis of the effect of S6F1 antibody on viral load, CD4+ numbers, CD8+ T-cell numbers, pharmacokinetic parameters and immunogenicity is presented below. Complete data by study subject is summarized in Table 2.

TABLE 2

Phase Ib/II Study Data

| PATIENT # DOSE LEVEL | SCREENING BASELINE | 28 DAYS FROM LAST INFUSION | VIRAL LOAD (LOG) CHANGE | VIRAL LOAD ABSOLUTE CHANGE |
|---|---|---|---|---|
| 3-1 | VL | 13,000 | | |
| .3 mg | CD4 | 326 | | |
| 3-2 | VL | 55,000 | 55,000 | 0.00 | 0 |
| .3 mg | CD4 | 221 | 252 | | |
| 3-3 | VL | 18,000 | 8,700 | (0.32) | (9.300) |
| .3 mg | CD4 | 529 | 635 | | |
| 3-4 | VL | 111,145 | 180,000 | 0.21 | 68,855 |
| .1 mg | CD4 | 379 | | | |
| | | Average VL Decrease | (0.04) | 19,852 |
| 4-1 | VL | 30,442 | 34,363 | 0.05 | 3,921 |
| 1 mg | CD4 | 289 | 162 | | |
| 4-2 | VL | 61,557 | 48,781 | (0.10) | (12,776) |
| 1 mg | CD4 | 415 | 393 | | |
| 4-3 | VL | 174,728 | 164,245 | (0.03) | (10,483) |
| 1 mg | CD4 | 335 | 396 | | |
| 4-4 | VL | 20,213 | 12,584 | (0.21) | (7,629) |
| 1 mg | CD4 | 484 | 426 | | |
| | | Average VL Decrease | (0.07) | (6,742) |
| 5-1 | VL | 200,813 | 428,049 | 0.33 | 227,236 |
| 2 mg | CD4 | 216 | 211 | | |
| 5-2 | VL | 38,524 | 3,345 | (1.06) | (35,179) |
| 2 mg | CD4 | 362 | 211 | | |
| 5-3 | VL | 126,116 | 2,625 | (1.68) | (123,491) |
| 2 mg | CD4 | 336 | 605 | | |
| 5-4 | VL | 86,041 | 11,751 | (0.86) | (74,290) |
| 2 mg | CD4 | 343 | 462 | | |
| 5-5 | VL | 242,690 | 169,936 | (0.15) | (72,754) |
| 2 mg | CD4 | 295 | 252 | | |
| | | Average VL Decrease | (0.69) | (15,696) |

Three patients in the 2 mg dose level group consented to additional testing to determine viral load 121 to 145 days from their last infusion. These results are shown in Table 3.

TABLE 3

Long Term Viral Load Values

| PATIENT # DOSE LEVEL | SCREENING BASELINE | | DAYS FROM LAST INFUSION | VIRAL LOAD (LOG) CHANGE | VIRAL LOAD ABSOLUTE CHANGE |
|---|---|---|---|---|---|
| 5-2 2 mg | VL CD4 | 38,254 362 | 145 | (0.63) | (29,486) |
| 5-3 2 mg | VL CD4 | 126,116 336 | 139 | (1.93) | (124,620) |
| 5-5 2 mg | VL CD4 | 242,690 295 | 121 | (0.21) | (94,403) |
| | | Average VL Decrease | | (0.92) | (82,836) |

Analysis of the data indicates that S6F1 antibody was safe and well tolerated. Overall, 100 treatment-emergent adverse events were reported (0.3 mg/kg: 15, 1.0 mg/kg: 19, 2.0 mg/kg multiple: 61, 2.0 mg/kg single: 5). Most treatment-emergent adverse events were considered mild (65%) or moderate (33%). Seventy-two percent of the treatment-emergent adverse events were considered by the investigator to be related to study drug (possible 20%, probable 51%, definite 1%). No treatment-emergent adverse events were considered serious. No patients withdrew because of adverse events and no patients died during the study.

HIV-1 RNA viral load was measured at baseline and at days 8, 29, and 50. The change from baseline (log) with increasing doses of S6F 1 antibody demonstrates a dose response (FIG. 1).

At the lowest dose (0.3 mg/kg) S6F1 antibody had no effect on reducing or maintaining HIV RNA viral load. In fact, HIV RNA viral load increased 1 week after a single infusion (day 8) and 1 week after 3 additional infusions (day 29). At the 1.0 mg/kg dose group, mean HIV RNA viral load decreased 0.24 log 1 week after a single infusion (day 8) and increased slightly 1 week after completion of 3 additional infusions (day 29).

A total of 5 patients received 2.0 mg/kg S6F1 antibody; 2 patients received a single infusion at day 1 and 3 patients received 4 weekly infusions. On day 8, 1 week after a single infusion, the mean decrease in HIV RNA viral load in the 2 patients who received a single 2.0 mg/kg S6F1 antibody infusion was 0.2 log compared with 0.8 log in the 3 patients who received 4 weekly infusions. When all patients who received 2.0 mg/kg S6 μl antibody are considered, the mean decrease in HIV RNA viral load on day 8 was 0.57 log. In the 2.0 mg/kg single infusion patients, HIV RNA viral load decreased further on day 29, 4 weeks after the single infusion. In the 2.0 mg/kg patients who received 4 weekly infusions, HIV RNA viral load decreased to approximately 1.0 log below baseline on day 29 and was maintained at this low level for 35 days after the last infusion. The percent decrease in HIV RNA viral load between days 8 and 29 for both single dose and multiple dose 2.0 mg/kg groups was similar (0.29 and 0.25 for the single and multiple dose groups, respectively), which suggests that the additional doses of S6F1 antibody do not appear to increase the rate (rate is defined as the decrease in HIV RNA viral load over time). However, the data indicate that additional doses of S6F1 antibody maintain the decrease in viral load after S6F1 antibody treatment ceases.

Figure 2:
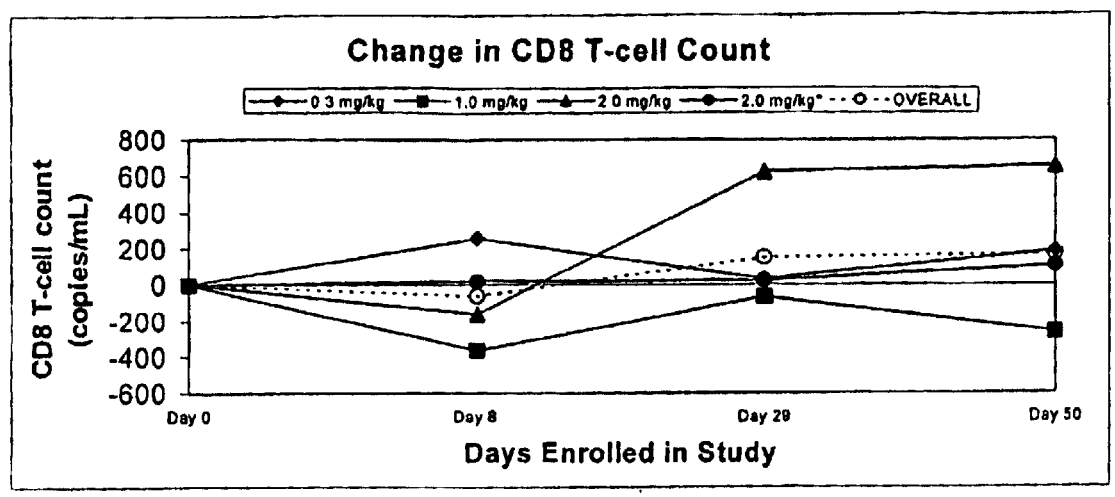
FIG. 2 shows the change from baseline for each dose group of S6F 1 antibody and for the overall patient population in the CD8+T cell counts measured at days 8, 29, and 50. 2.0 mg/kg* indicates 2.0 mg/kg single-dose group.

The CD8+ T cell numbers were measured at baseline and at days 8, 29, and 50. FIG. 2 displays the change from baseline for each dose group of S6F 1 antibody and for the overall patient population.

No dose relationship was observed on CD8+ T-cell numbers. Through the course of the study, CD8+ T-cell numbers fluctuated in all groups. One week after a single infusion (day 8) CD8+ T-cell count was highest in the 0.3 mg/kg dose group and lowest in the 1.0 mg/kg dose group. At the end of the study (day 50) CD8+ T-cell count was highest in the 2.0 mg/kg multiple infusion group (approximately 600 cells/mm$^3$ above baseline) and lowest in the 1.0 mg/kg dose group (approximately 300 cells/mm$^3$ below baseline). In both the 0.3 mg/kg dose group and the 2.0 mg/kg single infusion group CD8+ T-cell count was approximately 100 cells/mm$^3$ above baseline on day 50.

Figure 3:
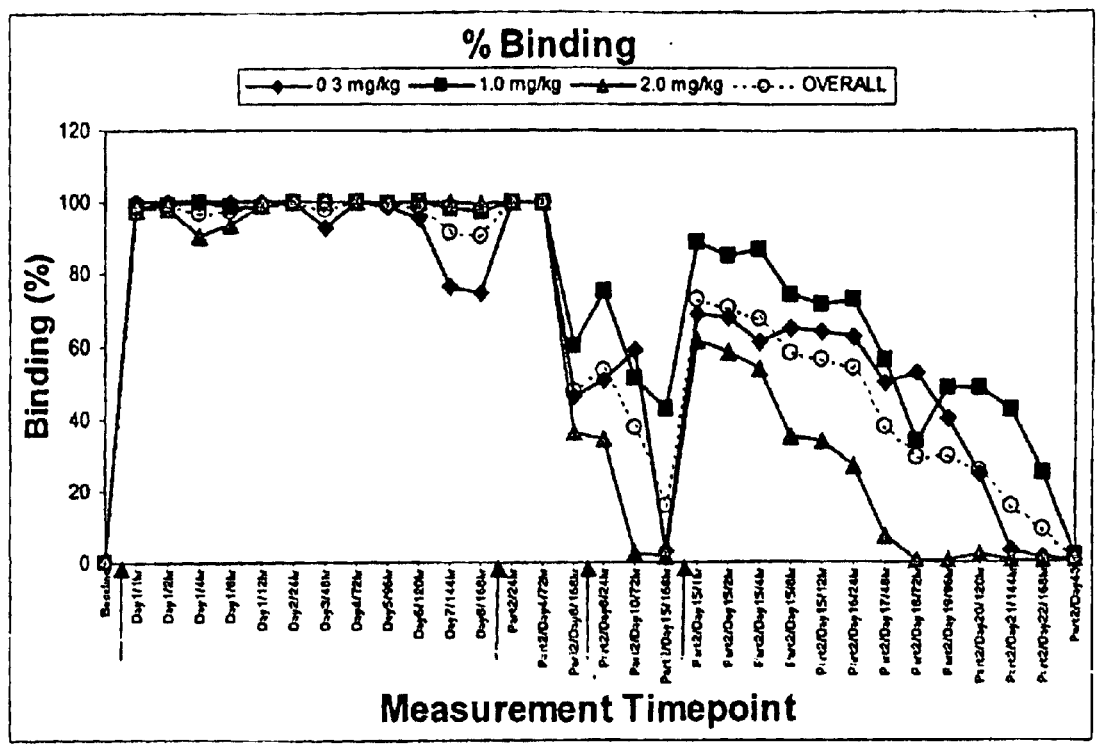
FIG. 3 shows the percent binding of multiple doses of S6F1 antibody at various time points through day 43.

The percent binding of the multiple doses of S6F1 antibody was measured at various time points through day 43 as shown in FIG. 3. The percent binding was approximately 100% following a single infusion in all dose groups. The degree of binding was constant for all dose groups after the first infusion except for the lowest dose, 0.3 mg/kg, where binding started to decrease at day 6. In all of the multiple-dose groups, the percent and duration of binding decreased with repeated infusions. In the 2.0 mg/kg single dose group percent binding was approximately 100% for 15 days after which it decreased to near 0% for the remainder of the study. The percent saturation fluctuated and was variable for all dose groups at all time points measured.

Human anti-mouse antibody (HAMA) was measured at baseline and at days 8, 29, and 50. No dose-response effect on HAMA was observed. In all dose groups, including the 2.0 mg/kg single-dose group, HAMA increased by day 29 at which point the mean levels of HAMA began to decrease in all treatment groups except in the 2.0 mg/kg multi-dose group where HAMA continued to rise. The largest increase from baseline HAMA was observed in the 2.0 mg/kg multiple-dose group. The degree and timing of HAMA corresponds to the decrease in binding seen in the 2.0 mg/kg and 1.0 mg/kg S6F1 antibody dose groups.

The data from both Phase I and Phase Ib/II human clinical trials indicate that S6F1 antibody decreases the HIV RNA viral load in a dose escalating fashion with the most significant decrease following infusion of 2.0 mg/kg S6F1 antibody. The decrease in viral load increase was greatest with multiple administrations of 2.0 mg/kg. However, the degree of decrease was similar to that seen with a single infusion of 2.0 mg/kg suggesting that multiple infusions of 2.0 mg/kg administered weekly may not increase the rate of further reduction in HIV RNA viral load but instead, maintain the decrease in viral load compared to lower S6F1 antibody doses.

The data also indicate that the decrease in viral load observed with 2.0 mg/kg was complemented by an increase in the CD4+ T cell counts. These data therefore demonstrate an effect of 2.0 mg/kg S6F1 antibody upon both viral load and CD4+ T cell counts.

After four infusions of 2.0 mg/kg (day 29 measurement), the increase from baseline HAMA was highest and the percent of binding was lowest. This contrasts with the 1.0 mg/kg S6F1 antibody where the increase from baseline HAMA was lowest and the percent binding was highest after four infusions (day 29). Given the relatively short duration of the study, it is difficult to assess the role of HAMA, if any, upon clinical efficacy since HAMA and the percent binding of S6F1 antibody did not correlate with effect on HIV RNA viral load and CD4+ T cell counts.

What is claimed is:

1. A method of treating a subject having or at risk of having a physiological condition associated with or caused by decreased CD4+ cell numbers, comprising administering to the subject an antibody that binds to LFA-1 alpha subunit (CD11a) in a unit dose amount of about 1.25 mg/kg body weight, or greater.

2. The method of claim 1, wherein the amount of antibody administered comprises between about 1.25 to 1.5, 1.5 to 1.75, 1.75 to 2.0, 2.0 to 2.5, 2.5 to 3.0, or 3.0 to 5.0 mg/kg body weight.

3. The method of claim 1, wherein the antibody inhibits binding of S6F1 antibody to LFA-1 alpha subunit.

4. The method of claim 1, wherein the antibody binds to an epitope to which S6F1 antibody binds.

5. The method of claim 4, wherein the epitope comprises an LFA-1 alpha subunit β-propeller domain.

6. The method of claim 4, wherein the antibody is a humanized form of S6F1.

7. The method of claim 4, wherein the epitope is located all or in a part of amino acids 1 to 57 of LFA-1 alpha subunit denoted as SEQ ID NO:2.

8. The method of claim 4, wherein the epitope is located all or in a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha subunit denoted as SEQ ID NO:2.

9. The method of claim 1, wherein the antibody is monoclanal.

10. The method of claim 9, wherein the antibody comprises S6F1.

11. The method of claim 1, wherein the antibody is a subsequence of full length antibody.

12. The method of claim 11, wherein the subsequence comprises Fab, Fab', (Fab)$_2$, Fv or scFv.

13. The method of claim 1, wherein the antibody that binds to LFA-1 alpha subunit is a humanized form.

14. The method of claim 13, wherein the humanized form has one or more amino acid substitutions, additions or deletions provided that said antibody has a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

15. The method of claim 1, wherein the antibody has a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

16. The method of claim 1, wherein the antibody comprises a fully human antibody having a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

17. The method of claim 1, wherein the antibody is administered systemically.

18. The method of claim 1, further comprising administering one or more additional doses of antibody that binds LFA-1 alpha subunit.

19. The method of claim 18, wherein one or more of the additional doses of antibody that binds to LFA-1 alpha is in an amount less than 1 mg/kg body weight.

20. The method of claim 18, wherein one more of the additional doses of antibody that binds to LFA-1 alpha is in an amount greater than 1 mg/kg body weight.

21. A method of increasing CD4+ cell numbers in a subject, comprising administering to the subject an antibody that binds to LFA-1 alpha subunit (CD11a) in a unit dose amount of about 1.25 mg/kg body weight, or greater.

22. The method of claim 21, wherein the amount of antibody administered comprises between about 1.25 to 1.5, 1.5 to 1.75, 1.75 to 2.0, 2.0 to 2.5, 2.5 to 3.0, or 3.0 to 5.0 mg/kg body weight.

23. The method of claim 21, wherein the antibody inhibits binding of S6F1 antibody to LFA-1 alpha subunit.

24. The method of claim 21, wherein the antibody binds to an epitope which S6F1 antibody binds.

25. The method of claim 21, wherein the epitope comprises an LEA-1 alpha subunit β-propeller domain.

26. The method of claim 22, wherein the antibody is a humanized form of S6F1.

27. The method of claim 21, wherein the epitope is located all or in a part of amino acids 1 to 57 of LFA-1 alpha subunit denoted as SEQ ID NO:2.

28. The method of claim 21, wherein the epitope is located all or in a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha subunit denoted as SEQ ID NO:2.

29. The method of claim 21, wherein the antibody is monoclanal.

30. The method of claim 29, wherein the antibody comprises S6F1.

31. The method of claim 21, wherein the antibody is a subsequence of full length antibody.

32. The method of claim 31, wherein the subsequence comprises Fab, Fab', (Fab)$_2$, Fv or scFv.

33. The method of claim 21, wherein the antibody that binds to LFA-1 alpha subunit comprises a humanized form of S6F1.

34. The method of claim 33, wherein the humanized form has one or more amino acid substitutions, additions or deletions provided that said antibody has a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

35. The method of claim 21, wherein the antibody has a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

36. The method of claim 21, wherein the antibody comprises a fully human antibody having a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

37. The method of claim 21, wherein the antibody is administered systemically.

38. The method of claim 21, further comprising administering one or more additional doses of antibody that binds to LFA-1 alpha subunit.

39. The method of claim 38, wherein one or more of the additional doses of antibody that binds to LFA-1 alpha is in an amount less than 1 mg/kg body weight.

40. The method of claim 38, wherein one or more of the additional doses of antibody that binds to LFA-1 alpha is in an amount greater than 1 mg/kg body weight.

41. A method of inhibiting or preventing decreases in CD4+ cell numbers in a subject, comprising administering to the subject an antibody that binds to LFA-1 alpha subunit (CD11a) in a unit dose amount of about 1.25 mg/kg body weight, or greater.

42. The method of claim 41, wherein the amount of antibody administered comprises between about 1.25 to 1.5, 1.5 to 1.75, 1.75 to 2.0, 2.0 to 2.5, 2.5 to 3.0, or 3.0 to 5.0 mg/kg body weight.

43. The method of claim 41, wherein the antibody inhibits binding of S6F1 antibody to LFA-1 alpha subunit.

44. The method of claim 41, wherein the antibody binds to an epitope which S6F1 antibody binds.

45. The method of claim 44, wherein the epitope comprises an LFA-1 alpha subunit β-propeller domain.

46. The method of claim 44, wherein the antibody is a humanized form of S6F1.

47. The method of claim 44, wherein the epitope is located all or in a part of amino acids 1 to 57 of LFA-1 alpha subunit denoted as SEQ ID NO:2.

48. The method of claim 44, wherein the epitope is located all or in a part of amino acids 1 to 5, 5 to 10, 10 to 15, 15 to 20, 20 to 25, 25 to 30, 35 to 40, 40 to 45, 45 to 50, 50 to 50 to 57 of LFA-1 alpha sununit denoted as SEQ ID NO:2.

49. The method of claim 41, wherein the anitbody is monoclonal.

50. The method of claim 49, wherein the anitbody comprises S6F1.

51. The method of claim 41, wherein the antibody is a subsequence of full length antibody.

52. The method of claim 51, wherein the subsequence comprises Fab, Fab', (Fab)$_2$, Fv or scFv.

53. The method of claim 41, wherein the antibody that binds to LFA-1 alpha subunit comprises a humanized form of S6F1.

54. The method of claim 53, wherein the humanized form has one or more amino acid substitutions, additions or deletions provided that said antibody has a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

55. The method of claim 41, wherein the antibody has a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

56. The method of claim 41, wherein the antibody comprises a fully human antibody having a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

57. The method of claim 41, wherein the antibody is administered systemically.

58. The method of claim 41, further comprising administering one or more additional doses of antibody that binds to LFA-1 alpha subunit.

59. The method of claim 58, wherein one or more of the additional doses of antibody that binds to LFA-1 alpha is in an amount less than 1 mg/kg body weight.

60. The method of claim 58, wherein one or more of the additional doses of antibody that binds to LFA-1 alpha is in an amount greater than 1 mg/kg body weight.

61. A method of treating a subject having or at risk of having a physiological condition treatable with an antibody that binds to LFA-1 alpha subunit (CD11a), comprising administering to the subject an antibody that binds to LFA-1 alpha subunit in a unit dose amount of about 1.25 mg/kg body weight, or greater.

62. The method of claim 61, wherein the amount of antibody administered comprises between about 1.25 to 1.5, 1.5 to 1.75, 1.75 to 2.0, 2.0 to 2.5, 2.5 to 3.0 or 3.0 to 5.0 mg/kg body weight.

63. The method of claim 61, wherein the antibody inhibits binding of S6F1 antibody to LFA-1 alpha subunit.

64. The method of claim 61, wherein the antibody binds to an epitope which S6F1 antibody binds.

65. The method of claim 64, wherein the epitope comprises an LFA-1 alpha subunit β-propeller domain.

66. The method of claim 64, wherein the antibody is a humanized form of S6F1.

67. The method of claim 64, wherein the epitope is located all or in a part of amino acids 1 to 57 of LFA-1 alpha denoted as SEQ ID NO:2.

68. The method of claim 64, wherein the epitope is located all or in a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha subunit denoted as SEQ ID NO:2.

69. The method of claim 61, wherein the antibody is monoclanal.

70. The method of claim 69, wherein the antibody comprises S6F1.

71. The method of claim 61, wherein the antibody is a subsequence of full length antibody.

72. The method of claim 71, wherein the subsequence comprises Fab, Fab', (Fab)$_2$, Fv or scFv.

73. The method of claim 61, wherein the antibody that binds to LFA-1 alpha subunit comprises a humanized form of S6F1.

74. The method of claim 73, wherein the humanized form has one or more amino acid substitutions, additions or deletions provided that said antibody has a binding affinity for LFA-1 alpha subunit or an epitope in LFA-1 alpha subunit within about 1 to 3, 2 to 5, 5 to 10, 10 to 50 or 10 to 100 fold treater or less than the binding affinity of S6F1.

75. The method of claim 61, wherein the antibody has a binding affinity for LFA-1 alpha subunit or an epitope in LFA-1 alpha subunit within about 1 to 3, 2 to 5, 5 to 10, 10 to 50 or 10 to 100 fold areater or less than the binding affinity of S6F1.

76. The method of claim 61, wherein the antibody comprises a fully human antibody having a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

77. The method of claim 61, wherein the antibody is administered systematically.

78. The method of claim 61, further comprising administering one or more additional doses of antibody that binds to LFA-1 alpha subunit.

79. The method of claim 78, wherein one or more of the additional doses of antibody that binds to LFA-1 alpha is in an amount less than 1 mg/kg body weight.

80. The method of claim 78, wherein one or more of the additional doses of antibody that binds to LFA-1 alpha is in an amount greater than 1 mg/kg body weight.

81. The method of treating a subject exposed to HIV or at risk of exposure to HIV, comprising administering to the subject an antibody that binds to LFA-1 alpha subunit (CD11a) in a unit dose amount of about 1.25 mg/kg body weight, or greater.

82. The method of claim 81, wherein the amount of antibody administered comprises between about 1.25 to 1.5, 1.5 to 1.75, 1.75 to 2.0, 2.0 to 2.5, 2.5 to 3.0, or 3.0 to 5.0 mg/kg body weight.

83. The method of claim 81, wherein the subject is asymptomatic or symptomatic for HIV infection.

84. The method of claim 81, wherein the subject has not been previously exposed to HIV.

85. The method of claim 81, wherein the antibody inhibits binding of S6F1 antibody to LFA-1 alpha subunit.

86. The method of claim 81, wherein the antibody binds to an epitope to which S6F1 antibody binds.

87. The method of claim 86, wherein the epitope comprises an LFA-1 alpha subunit β-propeller domain.

88. The method of claim 86, wherein the antibody is a humanized form of S6F1.

89. The method of claim 86, wherein the epitope is located all or in a part of amino acids 1 to 57 of LFA-1 alpha subunit denoted as SEQ ID NO: 2.

90. The method of claim 86, wherein the epitope is located all or in a part of amino acids 1 to 5, 5 to 10, 10 to 15, 15 to 20, 20 to 25, 25 to 30, 35 to 40, 40 to 45, 45 to 50, 50 to 55 or 50 to 57 of LFA-1 alpha subunit denoted as SEQ ID NO: 2.

91. The method of claim 81, wherein the antibody is monoclanal.

92. The method of claim 91, wherein the antibody comprises S6F1.

93. The method of claim 81, wherein the antibody is a subsequence of full length antibody.

94. The method of claim 93, wherein the subsequence comprises Fab, Fab', (Fab)$_2$, Fv or scFv.

95. The method of claim 81, wherein the antibody that binds to LFA-1 alpha subunit comprises a humanized form of S6F1.

96. The method of claim 95, wherein the humanized form has one or more amino acid substitutions, additions or deletions provided that said antibody has a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

97. The method of claim 81, wherein the antibody has a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

98. The method of claim 81, wherein the antibody comprises a fully human antibody having a binding affinity for LFA-1 alpha subunit or an epitope in LFA-1 alpha subunit within about 1 to 3, 2 to 5, 5 to 10, 10 to 50 or 10 to 100 fold greater or less than the binding affinity of S6F1.

99. The method of claim 81, wherein the antibody is administered systemically.

100. The method of claim 81, further comprising administering one or more additional doses of antibody that binds to LFA-1 alpha subunit.

101. The method of claim 100, wherein one or more of the additional doses of antibody that binds to LFA-1 alpha is in an amount less than 1 mg/kg body weight.

102. The method of claim 100, wherein one or more of the additional doses of antibody that binds to LFA-1 alpha is in an amount greater than 1 mg/kg body weight.

103. The method of claim 1, wherein the unit dose amount of antibody administered comprises 1.5 mg/kg body weight, or greater.

104. The method of claim 21, wherein the unit dose amount of antibody administered comprises 1.5 mg/kg body weight, or greater.

105. The method of claim 41, wherein the unit dose amount of antibody administered comprises 1.5 mg/kg body weight, or greater.

106. The method of claim 61, wherein the unit dose amount of antibody administered comprises 1.5 mg/kg body weight, or greater.

107. The method of claim 81, wherein the unit dose amount of antibody administered comprises 1.5 mg/kg body weight, or greater.

* * * * *

SEQUENCE LISTING

<160> NUMBER OF SEQ ID NOS: 3

<210> SEQ ID NO 1
<211> LENGTH: 1170
<212> TYPE: PRT
<213> ORGANISM: Homo sapiens

<400> SEQUENCE: 1

```
Met Lys Asp Ser Cys Ile Thr Val Met Ala Met Ala Leu Leu Ser Gly
 1               5                  10                  15

Phe Phe Phe Phe Ala Pro Ala Ser Ser Tyr Asn Leu Asp Val Arg Gly
             20                  25                  30

Ala Arg Ser Phe Ser Pro Pro Arg Ala Gly Arg His Phe Gly Tyr Arg
         35                  40                  45

Val Leu Gln Val Gly Asn Gly Val Ile Val Gly Ala Pro Gly Glu Gly
     50                  55                  60

Asn Ser Thr Gly Ser Leu Tyr Gln Cys Gln Ser Gly Thr Gly His Cys
 65                  70                  75                  80

Leu Pro Val Thr Leu Arg Gly Ser Asn Tyr Thr Ser Lys Tyr Leu Gly
                 85                  90                  95

Met Thr Leu Ala Thr Asp Pro Thr Asp Gly Ser Ile Leu Ala Cys Asp
            100                 105                 110

Pro Gly Leu Ser Arg Thr Cys Asp Gln Asn Thr Tyr Leu Ser Gly Leu
        115                 120                 125

Cys Tyr Leu Phe Arg Gln Asn Leu Gln Gly Pro Met Leu Gln Gly Arg
    130                 135                 140

Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
            180                 185                 190

Phe Ala Ala Val Gln Phe Ser Thr Ser Tyr Lys Thr Glu Phe Asp Phe
        195                 200                 205

Ser Asp Tyr Val Lys Trp Lys Asp Pro Asp Ala Leu Leu Lys His Val
    210                 215                 220

Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
                245                 250                 255

Lys Val Leu Ile Ile Ile Thr Asp Gly Glu Ala Thr Asp Ser Gly Asn
            260                 265                 270

Ile Asp Ala Ala Lys Asp Ile Ile Arg Tyr Ile Ile Gly Ile Gly Lys
        275                 280                 285

His Phe Gln Thr Lys Glu Ser Gln Glu Thr Leu His Lys Phe Ala Ser
    290                 295                 300

Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
            340                 345                 350

Gly Ile Ser Ala Asp Leu Ser Arg Gly His Ala Val Val Gly Ala Val
```

-continued

```
            355                 360                 365
Gly Ala Lys Asp Trp Ala Gly Gly Phe Leu Asp Leu Lys Ala Asp Leu
        370                 375                 380
Gln Asp Asp Thr Phe Ile Gly Asn Glu Pro Leu Thr Pro Glu Val Arg
385                 390                 395                 400
Ala Gly Tyr Leu Gly Tyr Thr Val Thr Trp Leu Pro Ser Arg Gln Lys
                405                 410                 415
Thr Ser Leu Leu Ala Ser Gly Ala Pro Arg Tyr Gln His Met Gly Arg
                420                 425                 430
Val Leu Leu Phe Gln Glu Pro Gln Gly Gly His Trp Ser Gln Val
        435                 440                 445
Gln Thr Ile His Gly Thr Gln Ile Gly Ser Tyr Phe Gly Gly Glu Leu
        450                 455                 460
Cys Gly Val Asp Val Asp Gln Asp Gly Glu Thr Glu Leu Leu Leu Ile
465                 470                 475                 480
Gly Ala Pro Leu Phe Tyr Gly Glu Gln Arg Gly Gly Arg Val Phe Ile
                485                 490                 495
Tyr Gln Arg Arg Gln Leu Gly Phe Glu Glu Val Ser Glu Leu Gln Gly
                500                 505                 510
Asp Pro Gly Tyr Pro Leu Gly Arg Phe Gly Glu Ala Ile Thr Ala Leu
                515                 520                 525
Thr Asp Ile Asn Gly Asp Gly Leu Val Asp Val Ala Val Gly Ala Pro
        530                 535                 540
Leu Glu Glu Gln Gly Ala Val Tyr Ile Phe Asn Gly Arg His Gly Gly
545                 550                 555                 560
Leu Ser Pro Gln Pro Ser Gln Arg Ile Glu Gly Thr Gln Val Leu Ser
                565                 570                 575
Gly Ile Gln Trp Phe Gly Arg Ser Ile His Gly Val Lys Asp Leu Glu
                580                 585                 590
Gly Asp Gly Leu Ala Asp Val Ala Val Gly Ala Glu Ser Gln Met Ile
        595                 600                 605
Val Leu Ser Ser Arg Pro Val Val Asp Met Val Thr Leu Met Ser Phe
        610                 615                 620
Ser Pro Ala Glu Ile Pro Val His Glu Val Glu Cys Ser Tyr Ser Thr
625                 630                 635                 640
Ser Asn Lys Met Lys Glu Gly Val Asn Ile Thr Ile Cys Phe Gln Ile
                645                 650                 655
Lys Ser Leu Tyr Pro Gln Phe Gln Gly Arg Leu Val Ala Asn Leu Thr
                660                 665                 670
Tyr Thr Leu Gln Leu Asp Gly His Arg Thr Arg Arg Arg Gly Leu Phe
                675                 680                 685
Pro Gly Gly Arg His Glu Leu Arg Arg Asn Ile Ala Val Thr Thr Ser
        690                 695                 700
Met Ser Cys Thr Asp Phe Ser Phe His Phe Pro Val Cys Val Gln Asp
705                 710                 715                 720
Leu Ile Ser Pro Ile Asn Val Ser Leu Asn Phe Ser Leu Trp Glu Glu
                725                 730                 735
Glu Gly Thr Pro Arg Asp Gln Arg Ala Gln Gly Lys Asp Ile Pro Pro
                740                 745                 750
Ile Leu Arg Pro Ser Leu His Ser Glu Thr Trp Glu Ile Pro Phe Glu
                755                 760                 765
Lys Asn Cys Gly Glu Asp Lys Lys Cys Glu Ala Asn Leu Arg Val Ser
        770                 775                 780
```

```
Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
                805                 810                 815

Val Gln Leu Asp Leu His Phe Pro Pro Gly Leu Ser Phe Arg Lys Val
            820                 825                 830

Glu Met Leu Lys Pro His Ser Gln Ile Pro Val Ser Cys Glu Glu Leu
        835                 840                 845

Pro Glu Glu Ser Arg Leu Leu Ser Arg Ala Leu Ser Cys Asn Val Ser
    850                 855                 860

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
                885                 890                 895

Asn Val Thr Cys Asn Asn Glu Asp Ser Asp Leu Leu Asp Asn Ser
            900                 905                 910

Ala Thr Thr Ile Ile Pro Ile Leu Tyr Pro Ile Asn Ile Leu Ile Gln
        915                 920                 925

Asp Gln Glu Asp Ser Thr Leu Tyr Val Ser Phe Thr Pro Lys Gly Pro
    930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
                965                 970                 975

Gln Pro Pro Ser Glu Gly Pro Ile Thr His Gln Trp Ser Val Gln Met
            980                 985                 990

Glu Pro Pro Val Pro Cys His Tyr Glu Asp Leu Glu Arg Leu Pro Asp
        995                 1000                1005

Ala Ala Glu Pro Cys Leu Pro Gly Ala Leu Phe Arg Cys Pro Val Val
    1010                1015                1020

Phe Arg Gln Glu Ile Leu Val Gln Val Ile Gly Thr Leu Glu Leu Val
1025                1030                1035                1040

Gly Glu Ile Glu Ala Ser Ser Met Phe Ser Leu Cys Ser Ser Leu Ser
                1045                1050                1055

Ile Ser Phe Asn Ser Ser Lys His Phe His Leu Tyr Gly Ser Asn Ala
            1060                1065                1070

Ser Leu Ala Gln Val Val Met Lys Val Asp Val Val Tyr Glu Lys Gln
        1075                1080                1085

Met Leu Tyr Leu Tyr Val Leu Ser Gly Ile Gly Gly Leu Leu Leu Leu
    1090                1095                1100

Leu Leu Ile Phe Ile Val Leu Tyr Lys Val Gly Phe Phe Lys Arg Asn
1105                1110                1115                1120

Leu Lys Glu Lys Met Glu Ala Gly Arg Gly Val Pro Asn Gly Ile Pro
                1125                1130                1135

Ala Glu Asp Ser Glu Gln Leu Ala Ser Gly Gln Glu Ala Gly Asp Pro
            1140                1145                1150

Gly Cys Leu Lys Pro Leu His Glu Lys Asp Ser Glu Ser Gly Gly Gly
        1155                1160                1165

Lys Asp
    1170

<210> SEQ ID NO 2
<211> LENGTH: 589
```

```
<212> TYPE: PRT
<213> ORGANISM: Homo sapiens

<400> SEQUENCE: 2

Tyr Asn Leu Asp Val Arg Gly Ala Arg Ser Phe Ser Pro Pro Arg Ala
  1               5                  10                  15

Gly Arg His Phe Gly Tyr Arg Val Leu Gln Val Gly Asn Gly Val Ile
             20                  25                  30

Val Gly Ala Pro Gly Glu Gly Asn Ser Thr Gly Ser Leu Tyr Gln Cys
         35                  40                  45

Gln Ser Gly Thr Gly His Cys Leu Pro Val Thr Leu Arg Gly Ser Asn
     50                  55                  60

Tyr Thr Ser Lys Tyr Leu Gly Met Thr Leu Ala Thr Asp Pro Thr Asp
 65                  70                  75                  80

Gly Ser Ile Leu Ala Cys Asp Pro Gly Leu Ser Arg Thr Cys Asp Gln
             85                  90                  95

Asn Thr Tyr Leu Ser Gly Leu Cys Tyr Leu Phe Arg Gln Asn Leu Gln
            100                 105                 110

Gly Pro Met Leu Gln Gly Arg Pro Gly Phe Gln Glu Cys Ile Lys Gly
        115                 120                 125

Asn Val Asp Leu Val Phe Leu Phe Asp Gly Ser Met Ser Leu Gln Pro
130                 135                 140

Asp Glu Phe Gln Lys Ile Leu Asp Phe Met Lys Asp Val Met Lys Lys
145                 150                 155                 160

Leu Ser Asn Thr Ser Tyr Gln Phe Ala Ala Val Gln Phe Ser Thr Ser
                165                 170                 175

Tyr Lys Thr Glu Phe Asp Phe Ser Asp Tyr Val Lys Trp Lys Asp Pro
            180                 185                 190

Asp Ala Leu Leu Lys His Val Lys His Met Leu Leu Leu Thr Asn Thr
        195                 200                 205

Phe Gly Ala Ile Asn Tyr Val Ala Thr Glu Val Phe Arg Glu Glu Leu
    210                 215                 220

Gly Ala Arg Pro Asp Ala Thr Lys Val Leu Ile Ile Ile Thr Asp Gly
225                 230                 235                 240

Glu Ala Thr Asp Ser Gly Asn Ile Asp Ala Ala Lys Asp Ile Ile Arg
                245                 250                 255

Tyr Ile Ile Gly Ile Gly Lys His Phe Gln Thr Lys Glu Ser Gln Glu
            260                 265                 270

Thr Leu His Lys Phe Ala Ser Lys Pro Ala Ser Glu Phe Val Lys Ile
        275                 280                 285

Leu Asp Thr Phe Glu Lys Leu Lys Asp Leu Phe Thr Glu Leu Gln Lys
    290                 295                 300

Lys Ile Tyr Val Ile Glu Gly Thr Ser Lys Gln Asp Leu Thr Ser Phe
305                 310                 315                 320

Asn Met Glu Leu Ser Ser Ser Gly Ile Ser Ala Asp Leu Ser Arg Gly
                325                 330                 335

His Ala Val Val Gly Ala Val Gly Ala Lys Asp Trp Ala Gly Gly Phe
            340                 345                 350

Leu Asp Leu Lys Ala Asp Leu Gln Asp Asp Thr Phe Ile Gly Asn Glu
        355                 360                 365

Pro Leu Thr Pro Glu Val Arg Ala Gly Tyr Leu Gly Tyr Thr Val Thr
    370                 375                 380

Trp Leu Pro Ser Arg Gln Lys Thr Ser Leu Leu Ala Ser Gly Ala Pro
385                 390                 395                 400
```

-continued

Arg Tyr Gln His Met Gly Arg Val Leu Leu Phe Gln Glu Pro Gln Gly
            405                 410                 415
Gly Gly His Trp Ser Gln Val Gln Thr Ile His Gly Thr Gln Ile Gly
        420                 425                 430
Ser Tyr Phe Gly Gly Glu Leu Cys Gly Val Asp Val Asp Gln Asp Gly
    435                 440                 445
Glu Thr Glu Leu Leu Ile Gly Ala Pro Leu Phe Tyr Gly Glu Gln
    450                 455                 460
Arg Gly Gly Arg Val Phe Ile Tyr Gln Arg Gln Leu Gly Phe Glu
465                 470                 475                 480
Glu Val Ser Glu Leu Gln Gly Asp Pro Gly Tyr Pro Leu Gly Arg Phe
            485                 490                 495
Gly Glu Ala Ile Thr Ala Leu Thr Asp Ile Asn Gly Asp Gly Leu Val
            500                 505                 510
Asp Val Ala Val Gly Ala Pro Leu Glu Glu Gln Gly Ala Val Tyr Ile
        515                 520                 525
Phe Asn Gly Arg His Gly Gly Leu Ser Pro Gln Pro Ser Gln Arg Ile
    530                 535                 540
Glu Gly Thr Gln Val Leu Ser Gly Ile Gln Trp Phe Gly Arg Ser Ile
545                 550                 555                 560
His Gly Val Lys Asp Leu Glu Gly Asp Gly Leu Ala Asp Val Ala Val
            565                 570                 575
Gly Ala Glu Ser Gln Met Ile Val Leu Ser Ser Arg Pro
        580                 585

<210> SEQ ID NO 3
<211> LENGTH: 5133
<212> TYPE: DNA
<213> ORGANISM: Homo sapiens

<400> SEQUENCE: 3
cctctttcac cctgtctagg ttgccagcaa atcccacggg cctcctgacg ctgcccctgg      60
ggccacaggt ccctcgagtg ctggaaggat gaaggattcc tgcatcactg tgatggccat     120
ggcgctgctg tctgggttct ttttcttcgc gccggcctcg agctacaacc tggacgtgcg     180
gggcgcgcgg agcttctccc caccgcgcgc cggggaggcac tttggatacc gcgtcctgca     240
ggtcggaaac ggggtcatcg tgggagctcc aggggagggg aacagcacag gaagcctcta     300
tcagtgccag tcgggcacag gacactgcct gccagtcacc ctgagaggtt ccaactatac     360
ctccaagtac ttgggaatga ccttggcaac agaccccaca gatggaagca ttttggcctg     420
tgaccctggg ctgtctcgaa cgtgtgacca gaacacctat ctgagtggcc tgtgttacct     480
cttccgccag aatctgcagg gtcccatgct gcagggcgc cctggttttc aggaatgtat     540
caagggcaac gtagacctgg tatttctgtt tgatggttcg atgagcttgc agccagatga     600
atttcagaaa attctggact tcatgaagga tgtgatgaag aaactcagca cacttcgta      660
ccagtttgct gctgttcagt tttccacaag ctacaaaaca gaatttgatt tctcagatta     720
tgttaaatgg aaggaccctg atgctctgct gaagcatgta aagcacatgt tgctgttgac     780
caatacctt ggtgccatca attatgtcgc gacagaggtg ttccgggagg agctgggggc     840
ccggccagat gccaccaaag tgcttatcat catcacggat gggaggcca ctgacagtgg     900
caacatcgat gcggccaaag acatcatccg ctacatcatc gggattggaa agcatttca      960
gaccaaggag agtcaggaga ccctccacaa atttgcatca aaaccgcga gcagtttgt     1020

```
gaaaattctg gacacatttg agaagctgaa agatctattc actgagctgc agaagaagat   1080
ctatgtcatt gagggcacaa gcaaacagga cctgacttcc ttcaacatgg agctgtcctc   1140
cagcggcatc agtgctgacc tcagcagggg ccatgcagtc gtgggggcag taggagccaa   1200
ggactgggct gggggctttc ttgacctgaa ggcagacctg caggatgaca catttattgg   1260
gaatgaacca ttgacaccag aagtgagagc aggctatttg gttacaccg tgacctggct    1320 gccctcccgg caaaagactt cgttgctggc ctcgggagcc cctcgatacc agcacatggg   1380
ccgagtgctg ctgttccaag agccacaggg cggaggacac tggagccagg tccagacaat   1440
ccatgggacc cagattggct cttatttcgg tggggagctg tgtggcgtcg acgtggacca   1500
agatggggag acagagctgc tgctgattgg tgccccactg ttctatgggg agcagagagg   1560
aggccgggtg tttatctacc agagaagaca gttgggttt gaagaagtct cagagctgca    1620 ggggacccc ggctacccac tcgggcggtt tggagaagcc atcactgctc tgacagacat    1680
caacggcgat gggctggtag acgtggctgt ggggcccct ctggaggagc aggggctgt     1740 gtacatcttc aatggggaggc acgggggct tagtccccag ccaagtcagc ggatagaagg   1800
gacccaagtg ctctcaggaa ttcagtggtt tggacgctcc atccatgggg tgaaggacct   1860
tgaaggggat ggcttggcag atgtggctgt ggggctgag agccagatga tcgtgctgag   1920
ctcccggccc gtggtggata tggtcaccct gatgtcctc tctccagctg agatcccagt    1980
gcatgaagtg gagtgctcct attcaaccag taacaagatg aaagaaggag ttaatatcac   2040
aatctgtttc cagatcaagt ctctctaccc ccagttccaa ggccgcctgg ttgccaatct   2100
cacttacact ctgcagctgg atggccaccg gaccagaaga cggggttgt tcccaggagg    2160 gagacatgaa ctcagaagga atatagctgt caccaccagc atgtcatgca ctgacttctc   2220
atttcatttc ccggtatgtg ttcaagacct catctccccc atcaatgttt ccctgaattt   2280 ctctcttttgg gaggaggaag ggacaccgag ggaccaaagg gcgcagggca aggacatacc   2340
gcccatcctg agaccctccc tgcactcgga aacctgggag atcccttttg agaagaactg   2400
tggggaggac aagaagtgtg aggcaaactt gagagtgtcc ttctctcctg caagatccag   2460
agccctgcgt ctaactgctt ttgccagcct ctctgtggag ctgagcctga gtaacttgga   2520
agaagatgct tactgggtcc agctggacct gcacttcccc ccgggactct ccttccgcaa   2580
ggtggagatg ctgaagcccc atagccagat acctgtgagc tgcgaggagc ttcctgaaga   2640
gtccaggctt ctgtccaggg cattatcttg caatgtgagc tctcccatct tcaaagcagg   2700
ccactcggtt gctctgcaga tgatgtttaa tacactggta aacagctcct gggggactc    2760 ggttgaattg cacgccaatg tgacctgtaa caatgaggac tcagacctcc tggaggacaa   2820
ctcagccact accatcatcc ccatcctgta ccccatcaac atcctcatcc aggaccaaga   2880
agactccaca ctctatgtca gtttcacccc caaaggcccc aagatccacc aagtcaagca   2940
catgtaccag gtgaggatcc agccttccat ccacgaccac aacatacccca cctggaggc    3000 tgtggttggg gtgccacagc ctcccagcga ggggcccatc acacaccagt ggagcgtgca   3060
gatggagcct cccgtgccct gccactatga ggatctggag aggctcccgg atgcagctga   3120
gccttgtctc cccggagccc tgttccgctg ccctgttgtc ttcaggcagg agatcctcgt   3180
ccaagtgatc gggactctgg agctggtggg agagatcgag gcctcttcca tgttcagcct   3240
ctgcagctcc ctctccatct ccttcaacag cagcaagcat ttccacctct atggcagcaa   3300
cgcctccctg gccaggttg tcatgaaggt tgacgtggtg tatgagaagc agatgctcta    3360
cctctacgtg ctgagcggca tcgggggggct gctgctgctg ctgctcattt tcatagtgct   3420
```

```
gtacaaggtt ggtttcttca aacggaacct gaaggagaag atggaggctg gcagaggtgt    3480
cccgaatgga atccctgcag aagactctga gcagctggca tctgggcaag aggctgggga    3540
tcccggctgc ctgaagcccc tccatgagaa ggactctgag agtggtggtg gcaaggactg    3600
agtccaggcc tgtgaggtgc agagtgccca gaactggact caggatgccc agggccactc    3660
tgcctctgcc tgcattctgc cgtgtgccct cgggcgagtc actgcctctc cctggccctc    3720
agtttcccta tctcgaacat ggaactcatt cctgaatgtc tcctttgcag gctcataggg    3780
aagacctgct gagggaccag ccaagagggc tgcaaaagtg agggcttgtc attaccagac    3840
ggttcaccag cctctcttgg ttccttcctt ggaagagaat gtctgatcta aatgtggaga    3900
aactgtagtc tcaggaccta gggatgttct ggccctcacc cctgccctgg gatgtccaca    3960
gatgcctcca cccccagaa cctgtccttg cacactcccc tgcactggag tccagtctct     4020
tctgctggca gaaagcaaat gtgacctgtg tcactacgtg actgtggcac acgccttgtt    4080
cttggccaaa gaccaaattc cttggcatgc cttccagcac cctgcaaaat gagaccctcg    4140
tggccttccc cagcctcttc tagagccgtg atgcctccct gttgaagctc tggtgacacc    4200
agcctttctc ccaggccagg ctccttcctg tcttcctgca ttcacccaga cagctccctc    4260
tgcctgaacc ttccatctcg cccacccctc cttccttgac cagcagatcc cagctcacgt    4320
cacacacttg gttgggtcct cacatctttc acacttccac caccctgcac tactccctca    4380
aagcacacgt catgtttctt catccggcag cctggatgtt ttttccctgt ttaatgattg    4440
acgtacttag cagctatctc tcagtgaact gtgagggtaa aggctatact tgtcttgttc    4500
accttgggat gacgccgcat gatatgtcag ggcgtgggac atctagtagg tgcttgacat    4560
aatttcactg aattaatgac agagccagtg ggaagataca gaaaaagagg gccggggctg    4620
ggcgcggtgg ttcacgcctg taatcccagc actttgggag gccaaggagg gtggatcacc    4680
tgaggtcagg agttagaggc cagcctggcg aaacccatc tctactaaaa atacaaaatc      4740
caggcgtggt ggcacacacc tgtagtccca gctactcagg aggttgaggt aggagaattg    4800
cttgaacctg ggaggtggag gttgcagtga gccaagattg cgccattgca ctccagcctg    4860
ggcaacacag cgagactccg tctcaaggaa aaataaaaa taaaagcgg gcacgggccc       4920 ggacatcccc acccttggag gctgtcttct caggctctgc cctgccctag ctccacaccc    4980
tctcccagga cccatcacgc ctgtgcagtg gccccacag aaagactgag ctcaaggtgg     5040
gaaccacgtc tgctaacttg gagccccagt gccaagcaca gtgcctgcat gtatttatcc    5100
aataaatgtg aaattctgtc caaaaaaaaa aaa                                 5133
```